(12) United States Patent
Kato et al.

(10) Patent No.: US 8,367,833 B2
(45) Date of Patent: Feb. 5, 2013

(54) PROCESS FOR PRODUCING 6-ARYLOXYQUINOLINE DERIVATIVE AND INTERMEDIATE THEREFOR

(75) Inventors: Yasuhito Kato, Kamisu (JP); Shizuo Shimano, Kamisu (JP); Akinori Morikawa, Kamisu (JP); Hiroki Hotta, Saitama (JP); Kazumi Yamamoto, Kamakura (JP); Nozomu Nakanishi, Yokohama (JP); Nobuto Minowa, Yokohama (JP); Hiroshi Kurihara, Ageo (JP)

(73) Assignees: Nippon Kayaku Co., Ltd., Tokyo-to (JP); Meiji Seika Pharma Co., Ltd., Tokyo-to (JP)

( * ) Notice: Subject to any disclaimer, the term of this patent is extended or adjusted under 35 U.S.C. 154(b) by 197 days.

(21) Appl. No.: 13/054,240

(22) PCT Filed: Jul. 13, 2009

(86) PCT No.: PCT/JP2009/062673
§ 371 (c)(1),
(2), (4) Date: Jan. 14, 2011

(87) PCT Pub. No.: WO2010/007964
PCT Pub. Date: Jan. 21, 2010

(65) Prior Publication Data
US 2011/0118468 A1  May 19, 2011

(30) Foreign Application Priority Data
Jul. 15, 2008  (JP) .................................. 2008-183930

(51) Int. Cl.
*C07D 215/38* (2006.01)
(52) U.S. Cl. ....................................................... 546/159
(58) Field of Classification Search ................... 546/159
See application file for complete search history.

(56) References Cited

U.S. PATENT DOCUMENTS

| | | | |
|---|---|---|---|
| 4,465,508 A | 8/1984 | Barton et al. | |
| 4,738,711 A | 4/1988 | Barton et al. | |
| 4,780,128 A | 10/1988 | Cartwright | |
| 2007/0203181 A1 | 8/2007 | Yamamoto et al. | |
| 2007/0219176 A1 | 9/2007 | Coulombe et al. | |

FOREIGN PATENT DOCUMENTS

| | | | |
|---|---|---|---|
| JP | 56-16461 | | 2/1981 |
| JP | 2008-110953 | | 5/2008 |
| WO | 2006/013896 | * | 2/2006 |
| WO | 2007/087717 | | 8/2007 |
| WO | 2007/088978 | | 8/2007 |

OTHER PUBLICATIONS

Supplementary European Search Report issued Sep. 27, 2011 in European Application No. 09797889.4.
International Search Report issued Aug. 11, 2009 in International (PCT) Application No. PCT/JP2009/062673.
K. Ogura, "Kagakusha no Tameno Kiso Koza 9 Yuki Jinmei Hanno", Feb. 10, 1998, p. 193, Niementowski Reaction (In Japanese).
M. Rosini et al., "Design, synthesis, and biological evaluation of substituted 2,3-dihydro-1*H*-cyclopenta[*b*]quinolin-9-ylamine related compounds as fructose-1,6-bisphosphatase inhibitors", Bioorganic & Medicinal Chemistry, vol. 14, pp. 7846-7853, 2006.
A. T. Vu et al., "ERβ ligands. Part 6: 6*H*-Chromeno[4,3-b]quinolines as a new series of estrogen receptor β-selective ligands", Bioorganic & Medicinal Chemistry Letters, vol. 17, pp. 4053-4056, 2007.
English translation of the International Preliminary Report on Patentability and Written Opinion dated Feb. 8, 2011.

* cited by examiner

*Primary Examiner* — D M Seaman
(74) *Attorney, Agent, or Firm* — Wenderoth, Lind & Ponack, L.L.P.

(57) ABSTRACT

Disclosed is a process for producing 6-aryloxyquinoline derivatives useful as insecticides or fungicides for agricultural and horticultural use. The process comprises a cyclization reaction step of reacting an anthranilic acid derivative represented by general formula (1) with a kenone in the presence of an acid to obtain a quinolone derivative and a condensation reaction step of reacting the quinolone derivative with a halogen compound or an acid anhydride to obtain a quinoline derivative.

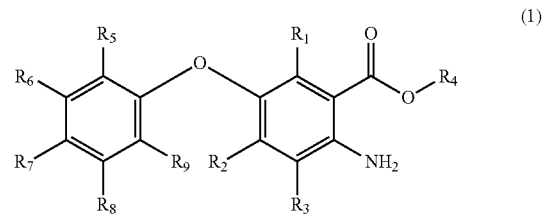

23 Claims, No Drawings

PROCESS FOR PRODUCING 6-ARYLOXYQUINOLINE DERIVATIVE AND INTERMEDIATE THEREFOR

This application is a U.S. national stage of International Application No. PCT/JP2009/062673 filed Jul. 13, 2009.

CROSS-REFERENCE OF RELATED APPLICATION

This application is based upon and claims the benefit of priority from the prior Japanese Patent Application No. 183930/2008 filed on Jul. 15, 2008, the entire contents of which are incorporated herein by reference.

FIELD OF INVENTION

The present invention relates to a process for producing a 6-aryloxyquinoline derivative useful as agricultural chemicals or pharmaceutical preparations, and a 4-aryloxyanthranilic acid derivative that is a synthetic intermediate suitable for the production process.

BACKGROUND ART

A brochure of International Publication No. 2006/013896 (patent document 1), Japanese Patent Application Laid-Open No. 110953/2008 (patent document 2), and a brochure of International Publication No. 2007/088978 (patent document 3) disclose that 6-aryloxyquinoline derivatives are compounds useful as agricultural and horticultural insecticides or agricultural and horticultural fungicides. These 6-aryloxyquinoline derivatives are compounds having high insecticidal activity against *Lepidoptera*, Hemiptera, Coleoptera, Acari, *Hymenoptera*, Orthoptera, Diptera, Order Thysanoptera, and plant parasitic nematodes.

Further, these 6-aryloxyquinoline derivatives are also effective as agricultural and horticultural fungicides against a variety of plant pathogenic fungi and are known as compounds having fungicidal effect, for example, against *Sphaerotheca fuliginea, Puccinia recondita, Erysiphe graminis, Alternaria solani, Venturia inaequalis, Monilinia fructicola*, and *Colletotrichum fragariae*.

The above documents disclose a process for producing a 6-aryloxyquinoline derivative in which a 4-aryloxyaniline derivative is reacted with a β-ketocarboxylic acid ester and a 6-aryloxyquinoline derivative is produced through a 6-aryloxyquinolone derivative. In this process, however, the yield in the cyclization reaction is low to medium. When the production of a derivative obtained by introducing a substituent into any one of the 5- and 7-positions of the quinoline derivative is contemplated, a mixture of a 5-position substitution product with a 7-position substitution product is obtained leading to a further lowering in yield of the contemplated compound and, at the same time, a complicated separation step of separating position isomers by column chromatography or the like is necessary. Accordingly, a process for producing a 6-aryloxyquinoline derivative, which can produce the 6-aryloxyquinoline derivative found as useful as insecticidal compounds and fungicidal compounds at a yield high enough to apply the process to the production of the 6-aryloxyquinoline derivative on a commercial scale, has been demanded.

PRIOR ART DOCUMENTS

Patent Documents

[Patent document 1] A brochure of International Publication No. 2006/013896

[Patent document 2] Japanese Patent Application Laid-Open No. 110953/2008

[Patent document 3] A brochure of International Publication No. 2007/088978

SUMMARY OF THE INVENTION

The present inventors have found that the use of a synthesis route through 4-aryloxyanthranilic acid derivatives in the production of 6-aryloxyquinoline derivatives can realize a significant improvement in the efficiency of a quinoline ring construction reaction and, at the same time, can realize regioselective introduction of a substituent into the 5- or 7-position of the 6-aryloxyquinoline derivative, whereby desired 6-aryloxyquinoline derivatives can be efficiently obtained at a high yield. The present inventors have further found a production process that can efficiently produce the 4-aryloxyanthranilic acid derivatives at a high yield. The present invention has been made based on these finding.

Accordingly, an object of the present invention is to provide a process for producing a 6-aryloxyquinoline derivative, and a process for producing a 4-aryloxyanthranilic acid derivative as an intermediate for the production of the 6-aryloxyquinoline derivative.

According to a first aspect of the present invention, there is provided a process for producing a quinoline derivative, the process comprising:

(i) a cyclization reaction step (C) of reacting an anthranilic acid derivative represented by general formula (1):

[Chemical formula 1]

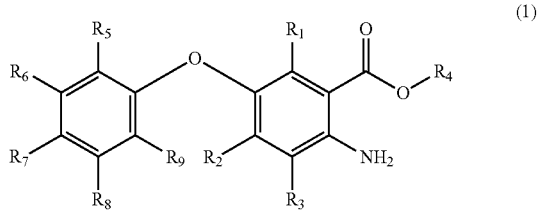

wherein $R_1$, $R_2$, and $R_3$ each independently represent a hydrogen atom, a halogen atom, $C_{1-4}$ alkyl optionally substituted by a halogen atom(s), or $C_{1-4}$ alkoxy optionally substituted by a halogen atom(s), provided that $R_1$, $R_2$, and $R_3$ do not simultaneously represent a hydrogen atom, $R_4$ represents a hydrogen atom or a protecting group of carboxylic acid, and, $R_5$, $R_6$, $R_7$, $R_8$, and $R_9$ each independently represent a hydrogen atom, a halogen atom, $C_{1-8}$ alkyl optionally substituted by a halogen atom(s), $C_{1-8}$ alkoxy optionally substituted by a halogen atom(s), $C_{1-8}$ alkylthio optionally substituted by a halogen atom(s), $C_{2-4}$ alkenyloxy optionally substituted by a halogen atom(s), $C_{2-4}$ alkenylthio optionally substituted by a halogen atom(s), or $C_{2-4}$ alkynyloxy optionally substituted by a halogen atom(s), or any two adjacent substituents of $R_5$, $R_6$, $R_7$, $R_8$, and $R_9$ together represent —O—$(CH_2)_n$—O—, wherein n is 1 or 2, optionally substituted by one or more halogen atoms, with a ketone represented by general formula (2):

[Chemical formula 2]

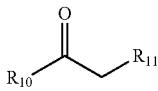

(2)

wherein $R_{10}$ and $R_{11}$ each independently represent a hydrogen atom or $C_{1-4}$ alkyl optionally substituted by a halogen atom(s), provided that $R_{10}$ and $R_{11}$ do not simultaneously represent a hydrogen atom, or $R_{10}$ and $R_{11}$ together represent —$(CH_2)_m$— wherein m is 3 or 4,
in the presence of an acid to obtain a quinolone derivative of general formula (3):

[Chemical formula 3]

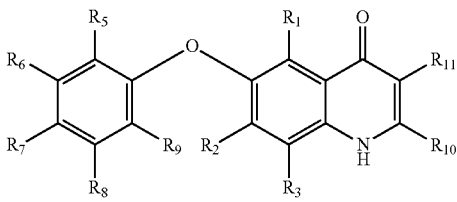

(3)

wherein $R_1$, $R_2$, $R_3$, $R_5$, $R_6$, $R_7$, $R_8$, $R_9$, $R_{10}$, and $R_{11}$ are as defined above; and (ii) a condensation reaction step (D) of reacting the quinolone derivative of general formula (3) with a halogen compound represented by general formula (4):

[Chemical formula 4]

$R_{12}COY$ (4)

wherein $R_{12}$ represents $C_{1-8}$ alkyl optionally substituted by a halogen atom(s), $C_{3-6}$ cyclic alkyl optionally substituted by a halogen atom(s), $C_{2-4}$ alkenyl optionally substituted by a halogen atom(s), $OR_{13}$ wherein $R_{13}$ represents $C_{1-8}$ alkyl optionally substituted by a halogen atom(s); $C_{3-6}$ cyclic alkyl optionally substituted by a halogen atom(s); or $C_{2-4}$ alkenyl optionally substituted by a halogen atom(s), or $SR_{14}$ wherein $R_{14}$ represents $C_{1-8}$ alkyl optionally substituted by a halogen atom(s); $C_{3-6}$ cyclic alkyl optionally substituted by a halogen atom(s); or $C_{2-4}$ alkenyl optionally substituted by a halogen atom(s), and Y represents any one of fluorine, chlorine, bromine, and iodine, or an acid anhydride represented by general formula (5):

[Chemical formula 5]

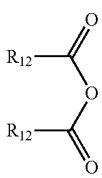

(5)

wherein $R_{12}$ is as defined above,
to obtain a quinoline derivative represented by general formula (6):

[Chemical formula 6]

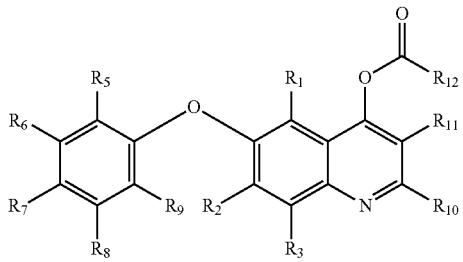

(6)

wherein $R_1$, $R_2$, $R_3$, $R_5$, $R_6$, $R_7$, $R_8$, $R_9$, $R_{10}$, $R_{11}$, and $R_{12}$ are as defined above.

According to a second aspect of the present invention, there is provided a process for producing an anthranilic acid derivative, the process comprising:

(i) an etherification step (A) of reacting a nitrobenzoic acid derivative represented by general formula (7):

[Chemical formula 7]

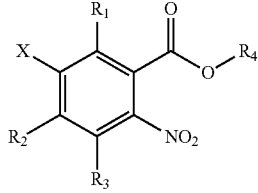

(7)

wherein
$R_1$, $R_2$, and $R_3$ each independently represent a hydrogen atom, a halogen atom, $C_{1-4}$ alkyl optionally substituted by a halogen atom(s), or $C_{1-4}$ alkoxy optionally substituted by a halogen atom(s), provided that $R_1$, $R_2$, and $R_3$ do not simultaneously represent a hydrogen atom, $R_4$ represents a hydrogen atom or a protecting group of carboxylic acid, and X represents any one of fluorine, chlorine, bromine, and iodine,
with a phenol derivative represented by general formula (8):

[Chemical formula 8]

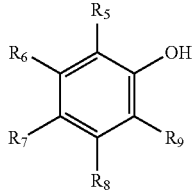

(8)

wherein
$R_5$, $R_6$, $R_7$, $R_8$, and $R_9$ each independently represent a hydrogen atom, a halogen atom, $C_{1-8}$ alkyl optionally substituted by a halogen atom(s), $C_{1-8}$ alkoxy optionally substituted by a halogen atom(s), $C_{1-8}$ alkylthio optionally substituted by a halogen atom(s), $C_{2-4}$ alkenyloxy optionally substituted by a halogen atom(s), $C_{2-4}$ alkenylthio optionally substituted by a halogen atom(s), or $C_{2-4}$ alkynyloxy optionally substituted by a halogen atom(s), or any two adjacent substituents of $R_5$, $R_6$, $R_7$, $R_8$, and $R_9$ together represent —O—$(CH_2)_n$—O—, wherein n is 1 or 2, optionally substituted by one or more halogen atoms, in the presence or absence of a base to obtain an ether derivative represented by general formula (9):

[Chemical formula 9]

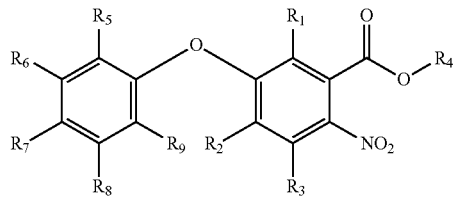

(9)

wherein $R_1$, $R_2$, $R_3$, $R_4$, $R_5$, $R_6$, $R_7$, $R_8$, and $R_9$ are as defined above; and (ii) a reduction step (B) of reducing the ether derivative of general formula (9) to obtain an anthranilic acid derivative represented by general formula (1):

[Chemical formula 10]

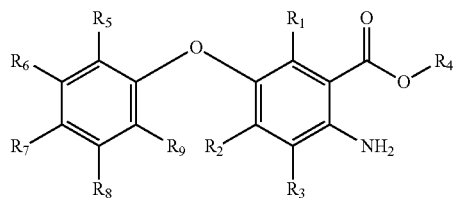

(1)

wherein $R_1$, $R_2$, $R_3$, $R_4$, $R_5$, $R_6$, $R_7$, $R_8$, and $R_9$ are as defined above.

According to a third aspect of the present invention, there is provided a process for producing a quinoline derivative, the process comprising the etherification step (A), the reduction step (B), the cyclization reaction step (C), and the condensation reaction step (D).

The anthranilic acid derivative represented by general formula (1) is an important intermediate in the production of a quinoline derivative represented by general formula (6), and novel compounds included in general formula (1) constituting one aspect of the present invention.

Thus, according to a fourth aspect of the present invention, there is provided an anthranilic acid derivative represented by general formula (1a):

[Chemical formula 11]

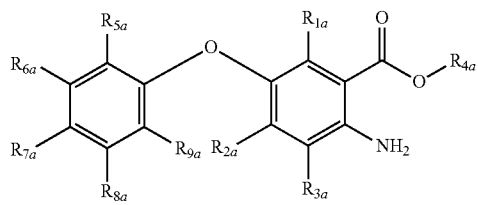

(1a)

wherein
any one of $R_{1a}$, $R_{2a}$, and $R_{3a}$ represents $C_{1-4}$ alkyl optionally substituted by a halogen atom(s) with the other two representing a hydrogen atom, $R_{4a}$ represents $C_{1-4}$ alkyl optionally substituted by a halogen atom(s), and, any one of $R_{5a}$, $R_{6a}$, $R_{7a}$, $R_{8a}$, and $R_{9a}$ represents $C_{1-8}$ alkoxy optionally substituted by a halogen atom(s) with the other four representing a hydrogen atom.

The present invention can realize the production of 6-aryloxyquinoline derivatives having high insecticidal activity or fungicidal activity at a high yield. According to the process of the present invention, the efficiency of the quinoline ring construction reaction is so high that 6-aryloxyquinoline derivatives can be efficiently produced at a high yield. Further, according to the process of the present invention, a substituent can be regioselectively introduced into all sites, of the quinoline ring, and, thus, desired quinoline derivatives that simultaneously have a variety of types of substituents at multiple sites can be selectively produced. Accordingly, the present invention can provide desired 6-aryloxyquinoline derivatives having a high purity without the need to provide a complicated isolation/purification step. Thus, the process according to the present invention is suitable for the mass production of specific 6-aryloxyquinoline derivatives and is industrially advantageous.

DETAILED DESCRIPTION OF THE INVENTION

Definition of Substituents in General Formulae

The term "halogen atom" as used herein means fluorine, chlorine, bromine, or iodine, preferably fluorine, chlorine, or bromine, more preferably chlorine or fluorine.

The term "cyclic alkyl" as used herein means that the alkyl group contains at least one cyclic structure. Examples of cyclic alkyl include cycloalkyl; and alkyl substituted by one or more cycloalkyls. These groups may be further substituted by one or more alkyl groups.

$C_{1-4}$ alkyl indicated by $R_1$, $R_2$, and $R_3$ may be of a straight chain or branched chain type, and examples thereof include methyl, ethyl, propyl, i-propyl, n-butyl, i-butyl, s-butyl, and t-butyl. Preferably, the $C_{1-4}$ alkyl represents straight chain $C_{1-4}$ alkyl, and examples thereof include methyl, ethyl, propyl, and n-butyl. More preferred is methyl or ethyl.

$C_{1-4}$ alkyl indicated by $R_1$, $R_2$, and $R_3$ is optionally substituted by a halogen atom(s). Examples of the $C_{1-4}$ alkyl substituted by a halogen atom(s) indicated by $R_1$, $R_2$, and $R_3$ include chloromethyl, trichloromethyl, trifluoromethyl, (1- or 2-)chloroethyl, 2,2,2-trifluoroethyl, 1,1,2,2-tetrafluoroethyl, and pentafluoroethyl and is preferably trifluoromethyl.

$C_{1-4}$ alkyl indicated by $R_1$, $R_2$, and $R_3$ is optionally substituted by $C_{1-4}$ alkoxy. Examples of the $C_{1-4}$ alkyl substituted by $C_{1-4}$ alkoxy indicated by $R_1$, $R_2$, and $R_3$ include methoxymethyl.

$C_{1-4}$ alkoxy indicated by $R_1$, $R_2$, and $R_3$ may be of a straight chain or branched chain type, and examples thereof include methoxy, ethoxy, n-propyloxy, n-butyloxy, i-propyloxy, i-butyloxy, s-butyloxy, and t-butyloxy. Preferably, the $C_{1-4}$ alkoxy represents straight chain $C_{1-4}$ alkoxy, and examples thereof include methoxy, ethoxy, n-propyloxy, and n-butyloxy. More preferred is methoxy or ethoxy.

$C_{1-4}$ alkoxy indicated by $R_1$, $R_2$, and $R_3$ is optionally substituted by a halogen atom(s). Examples of the $C_{1-4}$ alkoxy substituted by a halogen atom indicated by $R_1$, $R_2$, and $R_3$ include trifluoromethoxy, trichloromethoxy, difluoromethoxy, dichloromethoxy, 2,2,2-trifluoroethoxy, 2,2,2-trichloroethoxy, 1,1,2,2-tetrafluoroethoxy, pentafluoroethoxy, and pentachloroethoxy.

In a preferred embodiment of the present invention, $R_1$, $R_2$, and $R_3$ each independently represent a hydrogen atom, a chlorine atom, a bromine atom, a fluorine atom, methyl, ethyl, methoxy, ethoxy, or trifluoromethyl, provided that $R_1$, $R_2$, and $R_3$ do not simultaneously represent a hydrogen atom. More preferably, any one of $R_1$, $R_2$, and $R_3$ represents methyl, ethyl, or trifluoromethyl with the other two representing a hydrogen atom.

$R_4$ represents a hydrogen atom or a protecting group of carboxylic acid. Any protecting group of carboxylic acid known in the art may be used as the protecting group of carboxylic acid represented by $R_4$ without particular limitation. Specific examples of protecting group of carboxylic acids include $C_{1-8}$ alkyl optionally substituted by a halogen atom(s) or optionally substituted by $C_{1-4}$ alkoxy optionally substituted by a halogen atom(s); $C_{3-8}$ cyclic alkyl optionally substituted by a halogen atom(s); $C_{1-4}$ alkoxymethyl; benzoylmethyl optionally substituted by a halogen atom(s); or $C_{7-14}$ aralkyl optionally substituted by a halogen atom(s), $C_{1-4}$ alkyl, or $C_{1-4}$ alkoxy.

In a preferred embodiment of the present invention, $R_4$ represents $C_{1-8}$ alkyl optionally substituted by a halogen atom(s) or optionally substituted by $C_{1-4}$ alkoxy optionally substituted by a halogen atom(s); $C_{3-8}$ cyclic alkyl optionally substituted by a halogen atom(s); or $C_{7-14}$ aralkyl optionally substituted by a halogen atom(s), $C_{1-4}$ alkyl, or $C_{1-4}$ alkoxy. In a more preferred embodiment of the present invention, $R_4$ represents $C_{1-4}$ alkyl optionally substituted by a halogen atom(s).

$C_{1-8}$ alkyl indicated by $R_4$ may be of a straight chain or branched chain type, and examples thereof include methyl, ethyl, propyl, i-propyl, n-butyl, i-butyl, s-butyl, t-butyl, n-pentyl, (2- or 3-methyl)butyl, 2,3-dimethylpropyl, n-hexyl, (2,3, or 4-methyl)pentyl, (2,3-, 2,4-, or 3,4-dimethyl)butyl, 2,3,4-trimethylpropyl, n-heptyl, and n-octyl. Preferred is i-propyl.

$C_{1-8}$ alkyl indicated by $R_4$ is optionally substituted by a halogen atom(s). Examples of the $C_{1-8}$ alkyl substituted by a halogen atom(s) indicated by $R_4$ include chloromethyl, trichloromethyl, trifluoromethyl, (1- or 2-)chloroethyl, 2,2,2-trifluoroethyl, 1,1,2,2-tetrafluoroethyl, and pentafluoroethyl.

$C_{1-8}$ alkyl indicated by $R_4$ is optionally substituted by $C_{1-4}$ alkoxy optionally substituted by a halogen atom(s). Examples of the $C_{1-8}$ alkyl substituted by $C_{1-4}$ alkoxy optionally substituted by a halogen atom(s) indicated by $R_4$ include 2-trifluoromethoxyethyl.

Specific examples of $C_{3-8}$ cyclic alkyl optionally substituted by a halogen atom(s) indicated by $R_4$ include cyclopropylmethyl, cyclopropylethyl, cyclopropylpropyl, 1-methylcyclopropylmethyl, 2-(1-methylcyclopropyl)ethyl, 3-(1-methylcyclopropyl)propyl, 2,2-dimethylcyclopropylmethyl, 2-(2,2-dimethylcyclopropyl)ethyl, 3-(2,2-dimethylcyclopropyl)propyl, 2,2-dichlorocyclopropylmethyl, 2-(2,2-dichlorocyclopropyl)ethyl, 3-(2,2-dichlorocyclopropyl)propyl, 2,2-difluorocyclopropylmethyl, 2-(2,2-difluorocyclopropyl)ethyl, 3-(2,2-difluorocyclopropyl)propyl, cyclohexyl, cyclohexylmethyl, and cyclohexylethyl.

Specific examples of $C_{1-4}$ alkoxymethyl indicated by $R_4$ include methoxymethyl, ethoxymethyl, propyloxymethyl, and butoxymethyl.

Specific examples of benzoylmethyl optionally substituted by a halogen atom(s) indicated by $R_4$ include benzoylmethyl, chlorobenzoylmethyl, trichlorobenzoylmethyl, and pentachlorobenzoylmethyl.

Specific examples of $C_{7-14}$ aralkyl optionally substituted by a halogen atom(s), $C_{1-4}$ alkyl, or $C_{1-4}$ alkoxy indicated by $R_4$ include benzyl, 4-methylbenzyl, 2,4,6-trimethylbenzyl, 3-methoxybenzyl, 4-methoxybenzyl, 4-chlorobenzyl, and 2-phenylethyl. Preferred is benzyl.

$C_{1-8}$ alkyl indicated by $R_5$, $R_6$, $R_7$, $R_8$, and $R_9$ may be of a straight chain or branched chain type, and examples thereof include methyl, ethyl, propyl, i-propyl, n-butyl, i-butyl, s-butyl, t-butyl, n-pentyl, (2- or 3-methyl)butyl, 2,3-dimethylpropyl, n-hexyl, (2,3, or 4-methyl)pentyl, (2,3-, 2,4-, or 3,4-dimethyl)butyl, 2,3,4-trimethylpropyl, n-heptyl, and n-octyl. Preferred is methyl or ethyl.

$C_{1-8}$ alkyl indicated by $R_5$, $R_6$, $R_7$, $R_8$, and $R_9$ is optionally substituted by a halogen atom(s). Examples of the $C_{1-8}$ alkyl substituted by a halogen atom(s) indicated by $R_5$, $R_6$, $R_7$, $R_8$, and $R_9$ include chloromethyl, trichloromethyl, trifluoromethyl, (1- or 2-)chloroethyl, 2,2,2-trifluoroethyl, 1,1,2,2-tetrafluoroethyl, and pentafluoroethyl. Preferred is trifluoromethyl or pentafluoroethyl.

$C_{1-8}$ alkyl indicated by $R_5$, $R_6$, $R_7$, $R_8$, and $R_9$ is optionally substituted by $C_{1-4}$ alkoxy optionally substituted by a halogen atom(s). Examples of the $C_{1-8}$ alkyl that is substituted by $C_{1-4}$ alkoxy optionally substituted by a halogen atom(s) and is indicated by $R_5$, $R_6$, $R_7$, $R_8$, and $R_9$ include 2-trifluoromethoxyethyl.

$C_{1-8}$ alkoxy indicated by $R_5$, $R_6$, $R_7$, $R_9$, and $R_9$ may be of a straight chain or branched chain type, and examples thereof include methoxy, ethoxy, n-propyloxy, n-butyloxy, i-propyloxy, i-butyloxy, s-butyloxy, t-butyloxy, n-pentyloxy, (2- or 3-methyl)butyloxy, 2,3-dimethylpropyloxy, n-hexyloxy, (2,3, or 4-methyl)pentyloxy, (2,3-, 2,4-, or 3,4-dimethyl)butyloxy, 2,3,4-trimethylpropyloxy, n-heptyloxy, and n-octyloxy. Preferred is methoxy or ethoxy.

$C_{1-8}$ alkoxy indicated by $R_5$, $R_6$, $R_7$, $R_8$, and $R_9$ is optionally substituted by a halogen atom(s). Examples of the $C_{1-8}$ alkoxy substituted by a halogen atom(s) indicated by $R_5$, $R_6$, $R_7$, $R_8$, and $R_9$ include trifluoromethoxy, trichloromethoxy, difluoromethoxy, dichloromethoxy, 2,2,2-trifluoroethoxy, 2,2,2-trichloroethoxy, 1,1,2,2-tetrafluoroethoxy, pentafluoroethoxy, and pentachloroethoxy. Preferred is trifluoromethoxy, difluoromethoxy, or 1,1,2,2-tetrafluoroethoxy. More preferred is trifluoromethoxy or 1,1,2,2-tetrafluoroethoxy.

$C_{1-8}$ alkylthio indicated by $R_5$, $R_6$, $R_7$, $R_8$, and $R_9$ may be of a straight chain or branched chain type, and examples thereof include methylthio, ethylthio, n-propylthio, n-butylthio, i-propylthio, i-butylthio, s-butylthio, t-butylthio, n-pentylthio, (2- or 3-methyl)butylthio, 2,3-dimethylpropylthio, n-hexylthio, (2,3, or 4-methyl)pentylthio, (2,3-, 2,4-, or 3,4-dimethyl)butylthio, 2,3,4-trimethylpropylthio, n-heptylthio, and n-octylthio. Preferred is methylthio or ethylthio.

$C_{1-8}$ alkylthio indicated by $R_5$, $R_6$, $R_7$, $R_8$, and $R_9$ is optionally substituted by a halogen atom(s). Examples of the $C_{1-8}$ alkylthio substituted by a halogen atom(s) indicated by $R_5$, $R_6$, $R_7$, $R_8$, and $R_9$ include trifluoromethylthio, trichloromethylthio, difluoromethylthio, dichloromethylthio, trifluoroethylthio, trichloroethylthio, tetrafluoroethylthio, tetrachloroethylthio, pentafluoroethylthio, pentachloroethylthio, heptafluoro-n-propylthio, and heptafluoro-i-propylthio. Preferred is trifluoromethylthio, trichloromethylthio, difluoromethylthio, dichloromethylthio, trifluoroethylthio, trichloroethylthio, tetrafluoroethylthio, tetrachloroethylthio, heptafluoro-n-propylthio, or heptafluoro-i-propylthio. More preferred is trifluoromethylthio, difluoromethylthio, heptafluoro-n-propylthio, or heptafluoro-i-propylthio.

$C_{2-4}$ alkenyloxy indicated by $R_5$, $R_6$, $R_7$, $R_8$, and $R_9$ may be of a straight chain or branched chain type, and examples thereof include vinyloxy, (1- or 2-)propenyloxy, (1-, 2-, or 3-)butenyloxy, 1-methylvinyloxy, 1-methyl-1-propenyloxy, and 2-methyl-1-propenyloxy. Preferably, the $C_{2-4}$ alkenyloxy represents straight chain $C_{2-4}$ alkenyloxy, and examples thereof include vinyloxy, (1- or 2-)propenyloxy, and (1-, 2-, or 3-)butenyloxy.

$C_{2-4}$ alkenyloxy indicated by $R_5$, $R_6$, $R_7$, $R_8$, and $R_9$ is optionally substituted by a halogen atom(s). Examples of the $C_{2-4}$ alkenyloxy substituted by a halogen atom(s) indicated by $R_5$, $R_6$, $R_7$, $R_8$, and $R_9$ include 2-fluorovinyloxy, 2-chlorovinyloxy, 2,2-difluorovinyloxy, 2,2-dichlorovinyloxy, and 3,3-dichloro(1- or 2-)propenyloxy.

$C_{2-4}$ alkenyloxy indicated by $R_5$, $R_6$, $R_7$, $R_8$, and $R_9$ is optionally substituted by $C_{1-4}$ alkoxy optionally substituted by a halogen atom(s). Examples of the $C_{2-4}$ alkenyloxy substituted by $C_{1-4}$ alkoxy optionally substituted by a halogen atom(s) indicated by $R_5$, $R_6$, $R_7$, $R_8$, and $R_9$ include 2-trifluoromethoxyvinyloxy.

$C_{2-4}$ alkenylthio indicated by $R_5$, $R_6$, $R_7$, $R_8$, and $R_9$ may be of a straight chain or branched chain type, and examples thereof include vinylthio, (1- or 2-)propenylthio, (1-, 2-, or 3-)butenylthio, 1-methylvinylthio, 1-methyl-1-propenylthio, and 2-methyl-1-propenylthio. Preferably, the $C_{2-4}$ alkenylthio represents straight chain $C_{2-4}$ alkenylthio, and examples thereof include vinylthio, (1- or 2-)propenylthio, and (1-, 2-, or 3-)butenylthio.

$C_{2-4}$ alkenylthio indicated by $R_5$, $R_6$, $R_7$, $R_8$, and $R_9$ is optionally substituted by a halogen atom(s). Examples of the $C_{2-4}$ alkenylthio substituted by a halogen atom(s) indicated by $R_5$, $R_6$, $R_7$, $R_8$, and $R_9$ include 2-fluorovinylthio, 2-chlorovinylthio, 2,2-difluorovinylthio, and 2,2-dichlorovinylthio.

$C_{2-4}$ alkenylthio indicated by $R_5$, $R_5$, $R_7$, $R_8$, and $R_9$ is optionally substituted by $C_{1-4}$ alkoxy optionally substituted by a halogen atom(s). Examples of the $C_{2-4}$ alkenylthio substituted by $C_{1-4}$ alkoxy optionally substituted by a halogen atoms) indicated by $R_5$, $R_6$, $R_7$, $R_8$, and $R_9$ include 2-trifluoromethoxyvinylthio.

$C_{2-4}$ alkynyloxy indicated by $R_5$, $R_6$, $R_7$, $R_8$, and $R_9$ may be of a straight chain or branched chain type, and examples thereof include ethynyloxy, (1- or 2-)propynyloxy, (1-, 2-, or 3-)butynyloxy, 1-methylethynyloxy, 1-methyl-1-propynyloxy, and 2-methyl-1-propynyloxy. Preferably, the $C_{2-4}$ alkynyloxy represents straight chain $C_{2-4}$ alkynyloxy, and examples thereof include ethynyloxy, (1- or 2-)propynyloxy, and (1-, 2-, or 3-)butynyloxy.

$C_{2-4}$ alkynyloxy indicated by $R_5$, $R_6$, $R_7$, $R_8$, and $R_9$ is optionally substituted by a halogen atom(s). Examples of the $C_{2-4}$ alkynyloxy substituted by a halogen atom(s) indicated by $R_5$, $R_6$, $R_7$, $R_8$, and $R_9$ include fluoroethynyloxy, chloroethynyloxy, and 3-chloro(1- or 2-)propynyloxy.

Examples of $-O-(CH_2)_n-O-$, wherein n is 1 or 2, optionally substituted by one or more halogen atoms represented by combining any two adjacent substituents of $R_5$, $R_6$, $R_7$, $R_8$, and $R_9$ include $-O-(CF_2)_2-O-$, $-O-(CH_2)_2-O-$, $-O-CH_2CF_2-O-$, and $-O-CHFCF_2-O-$. Preferred is $-O-(CF_2)_2-O-$.

In a preferred embodiment of the present invention, $R_5$, $R_6$, $R_7$, $R_8$, and $R_9$ each independently represent a hydrogen atom, a chlorine atom, a bromine atom, a fluorine atom, methyl, ethyl, methoxy, ethoxy, trifluoromethyl, pentafluoroethyl, trifluoromethoxy, or 1,1,2,2-tetrafluoroethoxy, or $R_6$ and $R_7$ together may represent $-OCF_2CF_2O-$. In a more preferred embodiment of the present invention, any one of $R_5$, $R_6$, $R_7$, $R_8$, and $R_9$ represents methoxy, ethoxy, trifluoromethoxy, or 1,1,2,2-tetrafluoroethoxy with the other four representing a hydrogen atom.

$C_{1-4}$ alkyl indicated by $R_{10}$ and $R_{11}$ may be of a straight chain or branched chain type, and examples thereof include methyl, ethyl, propyl, i-propyl, n-butyl, i-butyl, s-butyl, and t-butyl. Preferred is methyl or ethyl.

$C_{1-4}$ alkyl indicated by $R_{10}$ and $R_{11}$ is optionally substituted by a halogen atom(s). Examples of the $C_{1-4}$ alkyl substituted by a halogen atom(s) indicated by $R_{10}$ and $R_{11}$ include chloromethyl, trichloromethyl, trifluoromethyl, (1- or 2-)chloroethyl, 2,2,2-trifluoroethyl, 1,1,2,2-tetrafluoroethyl, and pentafluoroethyl.

$C_{1-4}$ alkyl indicated by $R_{10}$ and $R_{11}$ is optionally substituted by $C_{1-4}$ alkoxy optionally substituted by a halogen atom(s). Examples of the $C_{1-4}$ alkyl substituted by $C_{1-4}$ alkoxy optionally substituted by a halogen atom(s) indicated by $R_{10}$ and $R_{11}$ include 2-trifluoromethoxyethyl.

In a preferred embodiment of the present invention, $R_{10}$ and $R_{11}$ each independently represent a hydrogen atom or $C_{1-4}$ alkyl optionally substituted by a halogen atom(s), provided that Rio and $R_{11}$ do not simultaneously represent a hydrogen atom. In a more preferred embodiment of the present invention, Ro and $R_{11}$ each independently represent $C_{1-4}$ alkyl optionally substituted by a halogen atom(s). In these embodiments, $C_{1-4}$ alkyl preferably represents straight chain $C_{1-4}$ alkyl.

In a more preferred embodiment of the present invention, Rio represents $-CH_2-R_{15}$, $R_{11}$ represents $R_{15}$, and $R_{15}$ represents $C_{1-3}$ alkyl. In this case, $C_{1-3}$ alkyl indicated by $R_{15}$ may be of a straight chain or branched chain type, preferably straight chain $C_{1-3}$ alkyl, more preferably methyl.

$C_{1-8}$ alkyl indicated by $R_{12}$, $R_{13}$, and $R_{14}$ may be of a straight chain or branched chain type, and examples thereof include methyl, ethyl, propyl, i-propyl, n-butyl, i-butyl, s-butyl, t-butyl, n-pentyl, (2- or 3-methyl)butyl, 2,3-dimethylpropyl, n-hexyl, (2,3, or 4-methyl)pentyl, (2,3-, 2,4-, or 3,4-dimethyl)butyl, 2,3,4-trimethylpropyl, n-heptyl, and n-octyl.

$C_{1-8}$ alkyl indicated by $R_{12}$, $R_{13}$, and $R_{14}$ is optionally substituted by a halogen atom(s). Examples of the $C_{1-8}$ alkyl substituted by a halogen atom(s) indicated by $R_{12}$, $R_{13}$, and $R_{14}$ include chloromethyl, trichloromethyl, trifluoromethyl, (1- or 2-)chloroethyl, 2,2,2-trifluoroethyl, 1,1,2,2-tetrafluoroethyl, and pentafluoroethyl.

$C_{1-8}$ alkyl indicated by $R_{12}$, $R_{13}$, and $R_{14}$ is optionally substituted by $C_{1-4}$ alkoxy optionally substituted by a halogen atom(s). Examples of the $C_{1-8}$ alkyl substituted by $C_{1-4}$ alkoxy optionally substituted by a halogen atom(s) indicated by $R_{12}$, $R_{13}$, and $R_{14}$ include 2-trifluoromethoxyethyl.

Specific examples of $C_{3-6}$ cyclic alkyl that is optionally substituted by a halogen atom(s) and is indicated by $R_{12}$, $R_{13}$, and $R_{14}$ include cyclopropylmethyl, cyclopropylethyl, cyclopropylpropyl, 1-methylcyclopropylmethyl, 2-(1-methylcyclopropyl)ethyl, 2,2-dimethylcyclopropylmethyl, 2,2-dichlorocyclopropylmethyl, 2-(2,2-dichlorocyclopropyl)ethyl, 3-(2,2-dichlorocyclopropyl)propyl, 2,2-difluorocyclopropylmethyl, 2-(2,2-difluorocyclopropyl)ethyl, 3-(2,2-difluorocyclopropyl)propyl, and cyclohexyl.

$C_{2-4}$ alkenyl indicated by $R_{12}$, $R_{13}$, and $R_{14}$ may be of a straight chain or branched chain type, and examples thereof include vinyl, (1- or 2-)propenyl, (1-, 2-, or 3-)butenyl, 1-methylvinyl, 1-methyl-1-propenyl, and 2-methyl-1-propenyl. Preferably, the $C_{2-4}$ alkenyl represents straight chain $C_{2-4}$ alkenyl, and examples thereof include vinyl, (1- or 2-)propenyl, and (1-, 2-, or 3-)butenyl.

$C_{2-4}$ alkenyl indicated by $R_{12}$, $R_{13}$, and $R_{14}$ is optionally substituted by a halogen atom(s). Examples of the $C_{2-4}$ alkenyl that is substituted by a halogen atom(s) and is indicated by $R_{12}$, $R_{13}$, and $R_{14}$ include 2-fluorovinyl, 2-chlorovinyl, 2,2-difluorovinyl, and 2,2-dichlorovinyl.

$C_{2-4}$ alkenyl indicated by $R_{12}$, $R_{13}$, and $R_{14}$ is optionally substituted by $C_{1-4}$ alkoxy optionally substituted by a halogen atom(s). Examples of the $C_{2-4}$ alkenyl substituted by $C_{1-4}$ alkoxy optionally substituted by a halogen atom(s) indicated by $R_{12}$, $R_{13}$, and $R_{14}$ include 2-trifluoromethoxyvinyl.

In a preferred embodiment of the present invention, $R_{12}$ represents $C_{1-4}$ alkyl optionally substituted by a halogen atom(s) or $OR_{13}$ wherein $R_{13}$ represents $C_{1-4}$ alkyl optionally substituted by a halogen atom(s). In a more preferred embodiment of the present invention, $R_{12}$ represents $OR_{13}$ wherein $R_{13}$ represents $C_{1-4}$ alkyl. In these embodiments, $C_{1-4}$ alkyl preferably represents straight chain $C_{1-4}$ alkyl, more preferably methyl.

$C_{1-4}$ alkyl indicated by $R_{1a}$, $R_{2a}$, and $R_{3a}$ may be of a straight chain or branched chain type, and examples thereof include methyl, ethyl, propyl, i-propyl, n-butyl, i-butyl, s-butyl, and t-butyl. Preferably, the $C_{1-4}$ alkyl indicated by $R_{1a}$, $R_{2a}$, and $R_{3a}$ represents straight chain $C_{1-4}$ alkyl. The $C_{1-4}$ alkyl indicated by $R_{4a}$ may be of a straight chain or branched chain type, and examples thereof include methyl, ethyl, propyl, i-propyl, n-butyl, i-butyl, s-butyl, and t-butyl and are preferably i-propyl. Further, these $C_{1-4}$ alkyl groups are optionally substituted by a halogen atom(s). Examples of $C_{1-4}$ alkyl optionally substituted by a halogen atom(s) include chloromethyl, trichloromethyl, trifluoromethyl, (1- or 2-)chloroethyl, 2,2,2-trifluoroethyl, 1,1,2,2-tetrafluoroethyl, and pentafluoroethyl.

$C_{1-8}$ alkoxy indicated by $R_{5a}$, $R_{6a}$, $R_{7a}$, $R_{8a}$, and $R_{9a}$ may be of a straight chain or branched chain type, and examples thereof include methoxy, ethoxy, n-propyloxy, n-butyloxy, i-propyloxy, i-butyloxy, s-butyloxy, t-butyloxy, n-pentyloxy, (t- or 3-methyl)butyloxy, 2,3-dimethylpropyloxy, n-hexyloxy, (2,3, or 4-methyl)pentyloxy, (2,3-, 2,4-, or 3,4-dimethyl)butyloxy, 2,3,4-trimethylpropyloxy, n-heptyloxy, and n-octyloxy. The $C_{1-8}$ alkoxy is optionally substituted by a halogen atom(s). Examples of $C_{1-8}$ alkoxy optionally substituted by a halogen atom(s) include trifluoromethoxy, trichloromethoxy, difluoromethoxy, dichloromethoxy, 2,2,2-trifluoroethoxy, 2,2,2-trichloroethoxy, 1,1,2,2-tetrafluoroethoxy, pentafluoroethoxy, and pentachloroethoxy.

The substituents $R_{1a}$ to $R_{9a}$ in general formula (1a) correspond respectively to substituents $R_1$ to $R_9$ in general formula (1). Accordingly, the preferred embodiments described above in connection with the substituents $R_1$ to $R_9$ can also be applied to the substituents $R_{1a}$ to $R_{9a}$.

In a preferred embodiment in connection with a combination of the substituents $R_1$ to $R_9$, $R_1$, $R_2$, and $R_3$ each independently represent a hydrogen atom, a chlorine atom, a bromine atom, a fluorine atom, methyl, ethyl, methoxy, ethoxy, or trifluoromethyl, provided that $R_1$, $R_2$, and $R_3$ do not simultaneously represent a hydrogen atom; $R_4$ represents $C_{1-8}$ alkyl optionally substituted by a halogen atom(s) or optionally substituted by $C_{1-4}$ alkoxy optionally substituted by a halogen atom(s); $C_{3-8}$ cyclic alkyl optionally substituted by a halogen atom(s); or $C_{7-14}$ aralkyl optionally substituted by a halogen atom(s), $C_{1-4}$ alkyl, or $C_{1-4}$ alkoxy, $R_5$, $R_6$, $R_7$, $R_8$, and $R_9$ each independently represent a hydrogen atom, a chlorine atom, a bromine atom, a fluorine atom, methyl, ethyl, methoxy, ethoxy, trifluoromethyl, pentafluoroethyl, trifluoromethoxy, or 1,1,2,2-tetrafluoroethoxy, or $R_6$ and $R_7$ together represent —OCF$_2$CF$_2$O—.

In a more preferred embodiment of the present invention, any one of $R_1$, $R_2$, and $R_3$ represents methyl, ethyl, or trifluoromethyl with the other two representing a hydrogen atom, $R_4$ represents $C_{1-4}$ alkyl optionally substituted by a halogen atom(s), and any one of $R_5$, $R_6$, $R_7$, $R_8$, and $R_9$ represents methoxy, ethoxy, trifluoromethoxy, or 1,1,2,2-tetrafluoroethoxy with the other four representing a hydrogen atom.

In a preferred embodiment of the present invention in connection with a combination of the substituents $R_1$ to $R_{12}$, $R_1$, $R_2$, and $R_3$ each independently represent a hydrogen atom, a chlorine atom, a bromine atom, a fluorine atom, methyl, ethyl, methoxy, ethoxy, or trifluoromethyl, provided that $R_1$, $R_2$, and $R_3$ do not simultaneously represent a hydrogen atom; $R_4$ represents $C_{1-8}$ alkyl optionally substituted by a halogen atom(s) or optionally substituted by $C_{1-4}$ alkoxy optionally substituted by a halogen atom(s); $C_{3-8}$ cyclic alkyl optionally substituted by a halogen atom(s), or $C_{7-14}$ aralkyl optionally substituted by a halogen atom(s), $C_{1-4}$ alkyl, or $C_{1-4}$ alkoxy; $R_5$, $R_6$, $R_7$, $R_8$, and $R_9$ each independently represent a hydrogen atom, a chlorine atom, a bromine atom, a fluorine atom, methyl, ethyl, methoxy, ethoxy, trifluoromethyl, pentafluoroethyl, trifluoromethoxy, or 1,1,2,2-tetrafluoroethoxy or $R_6$ and $R_7$ together represent —OCF$_2$CF$_2$O—, $R_{10}$ and $R_{11}$ each independently represent a hydrogen atom or $C_{1-4}$ alkyl optionally substituted by a halogen atom(s), provided that $R_{10}$ and $R_{11}$ do not simultaneously represent a hydrogen atom, and $R_{12}$ represents $C_{1-4}$ alkyl optionally substituted by a halogen atom(s) or $OR_{13}$ wherein $R_{13}$ represents $C_{1-4}$ alkyl optionally substituted by a halogen atom(s).

In a more preferred embodiment of the present invention, any one of $R_1$, $R_2$, and $R_3$ represents methyl, ethyl, or trifluoromethyl with the other two representing a hydrogen atom, $R_4$ represents $C_{1-4}$ alkyl optionally substituted by a halogen atom(s), any one of $R_5$, $R_6$, $R_7$, $R_8$, and $R_9$ represents methoxy, ethoxy, trifluoromethoxy, or 1,1,2,2-tetrafluoroethoxy with the other four representing a hydrogen atom, $R_{10}$ and $R_{11}$ each independently represent $C_{1-4}$ alkyl optionally substituted by a halogen atom(s), and $R_{12}$ represents $OR_{13}$ wherein $R_{13}$ represents $C_{1-4}$ alkyl.

Steps (A) to (D) Constituting Process of Present Invention

In the process according to the present invention, anthranilic acid derivatives represented by general formula (1) as important intermediates can be obtained by carrying out an etherification step (A) of reacting a nitrobenzoic acid derivative represented by general formula (7) with a phenol derivative represented by general formula (8) in the presence or absence of a base to give an ether derivative represented by general formula (9) and then a reduction step (B) of reducing the ether derivative to give an anthranilic acid derivative represented by general formula (1). Further, quinoline derivatives represented by general formula (6) useful as agricultural and horticultural insecticides or agricultural and horticultural fungicides can be obtained by carrying out, subsequently to the reduction step (B) or using the anthranilic acid derivative represented by general formula (1) as a starting compound, a cyclization reaction step (C) of reacting the anthranilic acid derivative with a ketone represented by general formula (2) in the presence of an acid to give a quinolone derivative represented by general formula (3) and then a condensation reaction step (D) of reacting the resultant quinolone derivative with a halogen compound represented by general formula (4) or an acid anhydride represented by general formula (5) to give a quinoline derivative represented by general formula (6). Each of steps (A) to (D) will be described.

Etherification Step (A)

The etherification step (A) is a step of reacting a nitrobenzoic acid derivative represented by general formula (7) with a phenol derivative represented by general formula (8) in the presence or absence of a base to give an ether derivative represented by general formula (9). The etherification step (A) is preferably carried out in the presence of a base.

Specific examples of ether derivatives represented by general formula (9) include methyl 4-methyl-2-nitro-5-(4-trifluoromethoxyphenoxy)benzoate, ethyl 4-methyl-2-nitro-5-(4-trifluoromethoxyphenoxy)benzoate, isopropyl 4-methyl-2-nitro-5-(4-trifluoromethoxyphenoxy)benzoate, methyl 2,4-dimethyl-6-nitro-3-(4-trifluoromethoxyphenoxy)benzoate, methyl 4-methyl-2-nitro-5-(4-(1,1,2,2-tetrafluoroethoxy)phenoxy)benz oate, methyl 4-methyl-2-nitro-5-(2,2,3,3-tetrafluoro-2,3-dihydrobenzodioxin-6-yloxy)benzoate, methyl 5-(2-chloro-4-trifluoromethoxyphenoxy)-4-methyl-2-nitrobenzoate, methyl 4-methoxy-2-nitro-5-(4-(1,1,2,2-tetrafluoroethoxy)phenoxy)benzoate, methyl 4-methoxy-2-nitro-5-(2,2,3,3-tetrafluoro-2,3-dihydrobenzodioxin-6-yloxy)benzoate, ethyl 4-methoxy-2-nitro-5-(2,2,3,3-tetrafluoro-2,3-dihydrobenzodioxin-6-yloxy)benzoate, isopropyl 4-methoxy-2-nitro-5-(2,2,3,3-tetrafluoro-2,3-dihydrobenzodioxin-6-yloxy)benzoate, methyl 4-fluoro-5-(4-trifluoromethoxyphenoxy)-2-nitrobenzoate, methyl 2-chloro-3-(4-chlorophenoxy)-6-nitrobenzoate, methyl 4-chloro-5-(4-chlorophenoxy)-2-nitrobenzoate, methyl 6-nitro-3-(4-(trifluoromethoxyphenoxy)-2-trifluoromethylbenzoate, methyl 2-nitro-5-(4-(trifluoromethoxyphenoxy)-4-trifluoromethylbenzoate, methyl 3-(2-chloro-4-trifluoromethylphenoxy)-6-nitro-2-trifluoromethyl benzoate, methyl 3-(2-chloro-4-trifluoromethylphenoxy)-6-nitro-4-trifluoromethyl benzoate, methyl 2-chloro-3-(4-methoxyphenoxy)-6-nitrobenzoate, methyl 4-chloro-5-(4-methoxyphenoxy)-2-nitrobenzoate, methyl 2-methyl-6-nitro-3-(4-trifluoromethoxyphenoxy)benzoate, methyl 3-(4-(3,3-dichloroallyloxyphenoxy)-2,4-dimethyl-6-nitrobenzoate, methyl 3-(4-(3-chloro-2-propynyloxy)phenoxy)-2,4-dimethyl-6-nitrobenzoate, methyl 2,4-dimethoxy-6-nitro-3-(4-trifluoromethoxyphenoxy) benzoate, methyl 4-fluoro-2-nitro-5-(4-perfluoro-2-propanethio)phenoxybenzoate, benzyl 4-methyl-2-nitro-5-(4-trifluoromethoxyphenoxy)benzoate, phenethyl 4-methyl-2-nitro-5-(4-trifluoromethoxyphenoxy)benzoate, cyclohexyl 4-methyl-2-nitro-5-(4-trifluoromethoxyphenoxy)benzoate, benzyl 4-methoxy-2-nitro-5-(2,2,3,3-tetrafluoro-2,3-dihydrobenzodioxin-6-yloxy)benzoate, cyclohexylmethyl 4-methoxy-2-nitro-5-(2,2,3,3-tetrafluoro-2,3-dihydrobenzodioxin-6-yloxy)benzoate, isopropyl 4-methyl-2-nitro-5-(4-(1,1,2,2-tetrafluoroethoxy)phenoxy)benz oate, benzyl 4-methyl-2-nitro-5-(4-(1,1,2,2-tetrafluoroethoxy)phenoxy)benz oate, benzyl 4-methoxy-2-nitro-5-(4-(1,1,2,2-tetrafluoroethoxy)phenoxy)benzoate, and isopropyl 4-fluoro-5-(4-trifluoromethoxyphenoxy)-2-nitrobenzoate.

The etherification step (A) is carried out in the presence or absence of a solvent. The solvent used is not particularly limited, and any solvent may be used as long as the solvent is not detrimental to the reaction. Such solvents include, for example, aliphatic hydrocarbons such as pentane, hexane, heptane, 2-methylbutane, 2-methylpentane, 2-methylhexane, cyclopentane, cyclohexane, and cycloheptane; halogenated aliphatic hydrocarbons such as methylene chloride, chloroform, and dichloroethane; aromatic hydrocarbons such as benzene, toluene, xylene, and mesitylene; halogenated aromatic hydrocarbons such as chlorobenzene and dichlorobenzene; ethers such as diisopropylether, tetrahydrofuran, and dioxane; alcohols such as methanol, ethanol, isopropyl alcohol, 2-butyl alcohol, and t-butyl alcohol; organic carboxylic acids such as acetic acid and propionic acid; amides such as dimethylformamide and dimethylacetamide; and water. The amount of the solvent used is preferably 2 to 50 times by mass, further preferably 2 to 10 times by mass, that of the nitrobenzoic acid derivative. These solvents may be used solely or in a combination of two or more of the solvents.

The etherification step (A) is carried out in the presence or absence of a base. Bases usable herein include, for example, inorganic bases such carbonates or hydroxides of alkali metals or alkaline earth metals; organic bases such as nitrogen-containing organic bases; metal alkoxides; and metal hydrides. Preferred is potassium carbonate, sodium carbonate, calcium carbonate, sodium hydrogen carbonate, sodium hydroxide, pyridine, triethylamine, sodium methoxide, sodium ethoxide, sodium butoxide, or sodium hydride. The amount of the base used is preferably 0 to 5.0 times by mole, more preferably 0.5 to 2.0 times by mole, that of the phenol derivative.

In the etherification step (A), preferably, the nitrobenzoic acid derivative is brought into contact with the phenol derivative in a liquid phase in the presence of a base. For example, the etherification step (A) is carried out, for example, by a method in which, in an inert gas atmosphere under normal pressure, applied pressure, or reduced pressure, the base, the nitrobenzoic acid derivative, the phenol derivative, and the solvent are mixed together and the mixture is heated with stirring. The reaction temperature is preferably 50 to 200° C., more preferably 80 to 150° C. The phenol derivative may be used in the form of a salt formed with the base.

The ether derivative obtained as a main product by the etherification step (A) as such may be used in the subsequent reduction step (B) without any post-treatment after the completion of the reaction, or alternatively may be used in the subsequent reduction step (B) after isolation/purification by simple and conventional post treatment such as extraction, distillation, or precipitation and, if necessary, separation/isolation by a method such as recrystallization or column chromatography.

Reduction Step (B)

The reduction step (B) is a step of reducing an ether derivative represented by general formula (9) to give an anthranilic acid derivative represented by general formula (1).

In the reduction step (B), the reduction reaction is not particularly limited and may be carried out by any conventional reduction method in which nitro group is converted to amino group. Examples of such reduction methods include reduction with an aluminum hydride compound, reduction with hydrogen in the presence of Raney nickel, reduction with hydrogen in the presence of palladium, reduction with iron powder, and reduction with stannous chloride. In a preferred embodiment of the present invention, the reduction in the reduction step (B) is carried out either by hydrogenation in the presence of palladium, or using iron powder.

The reduction reaction in the reduction step (B) is carried out in the presence or absence of a solvent.

Any solvent may be used without particular limitation as long as the solvent is not detrimental to the reaction. Such solvents include, for example, water; alcohols such as methanol, ethanol, and propanol; aromatic hydrocarbons such as benzene, toluene, and xylene; ethers such as diisopropylether and tetrahydrofuran; and amides such as dimethylformamide and dimethylacetamide. Preferred is water or alcohols. More preferred is water, methanol, or ethanol. The amount of the solvent used is preferably 2 to 50 times by mass, more preferably 3 to 20 times by mass, that of the ether derivative. These solvents may be used solely or in a combination of two or more of the solvents.

In the reduction reaction in the reduction step (B), preferably, the ether derivative is reacted in a liquid phase in the presence of a catalyst. For example, the reduction is carried out, for example, by a method in which, in a hydrogen atmosphere under the normal pressure or applied pressure, the ether derivative, palladium carbon, and methanol are mixed together, and the mixture is heated with stirring. The reaction temperature is preferably 20 to 110° C., more preferably 30 to 80° C.

The anthranilic acid derivative obtained as a main product by the reduction step (B) as such may be used in the subsequent cyclization reaction step (C) without any post-treatment after the completion of the reaction, or alternatively may be used in the subsequent cyclization reaction step (C) after isolation/purification by simple and conventional post treatment such as extraction, distillation, or precipitation and, if necessary, separation/isolation by a method such as recrystallization or column chromatography.

Cyclization Reaction Step (C)

The cyclization reaction step (C) is a step of reacting a ketone represented by general formula (2) with the anthranilic acid derivative represented by general formula (1) in the presence of an acid to give a quinolone derivative represented by general formula (3).

Examples of acids used in the cyclization reaction step (C) include organic sulfonic acids such as methanesulfonic acid, ethanesulfonic acid, benzenesulfonic acid, p-bromobenzenesulfonic acid, p-toluenesulfonic acid, and camphorsulfonic acid; Lewis acids such as zinc chloride, iron chloride, aluminum chloride, tin chloride, titanium chloride, boron fluoride, and boron chloride; inorganic acids such as phosphoric acid, pyrophosphoric acid, polyphosphoric acid, sulfuric acid, and hydrochloric acid; and halogenated organic carboxylic acids such as monochloroacetic acid, dichloroacetic acid, and trifluoroacetic acid. Preferred is an organic sulfonic acid or Lewis acid. The organic sulfonic acid is preferably benzenesulfonic acid or p-toluenesulfonic acid. The Lewis acid is preferably zinc chloride, iron chloride, titanium chloride, or aluminum chloride. The amount of the acid used is preferably 0.1 to 5.0 times by mole, more preferably 0.5 to 3.0 times by mole, that of the anthranilic acid derivative.

The cyclization reaction step (C) is carried out in the presence or absence of a solvent. The solvent used is not particularly limited as long as the solvent is not detrimental to the reaction. Such solvents include, for example, aliphatic hydrocarbons such as pentane, hexane, heptane, 2-methylbutane, 2-methylpentane, 2-methylhexane, cyclopentane, cyclohexane, and cycloheptane; halogenated aliphatic hydrocarbons such as methylene chloride, chloroform, and dichloroethane; aromatic hydrocarbons such as benzene, toluene, xylene, and mesitylene; halogenated aromatic hydrocarbons such as chlorobenzene and dichlorobenzene; ethers such as diisopropylether, tetrahydrofuran, and dioxane; alcohols such as methanol, ethanol, isopropyl alcohol, 2-butyl alcohol, and t-butyl alcohol; and organic carboxylic acids such as acetic acid and propionic acid. The amount of the solvent used is preferably 2 to 50 times by mass, more preferably 3 to 10 times by mass, that of the anthranilic acid derivative. These solvents may be used solely or in a combination of two or more of the solvents.

In the cyclization reaction step (C), preferably, the ketone is brought into contact with the anthranilic acid derivative in a liquid phase in the presence of an acid. For example, the cyclization is carried out, for example, by a method in which, in an inert gas atmosphere under the normal pressure, applied pressure, or reduced pressure, the acid, the ketone, the anthranilic acid derivative, and the solvent are mixed together, and the mixture is heated with stirring. The reaction temperature is preferably 50 to 200° C., more preferably 80 to 150° C. If necessary, the cyclization reaction step (C) may be carried out while removing water produced in the reaction. The anthranilic acid derivative may be used in the form of a salt formed with the acid.

Examples of ketones represented by general formula (2) include acetone, methyl ethyl ketone, methyl propyl ketone, methyl isobutyl ketone, 3-pentanone, ethyl butyl ketone, ethyl propyl ketone, cyclohexyl ethyl ketone, ethyl hexyl ketone, cyclohexenone, cyclopentanone, methylheptafluoro propyl ketone, and pentafluoroethyl ethyl ketone. Preferred is acetone, methyl ethyl ketone, or 3-pentanone.

The quinoline derivative obtained as a main product by the cyclization reaction step (C) as such may be used in the subsequent condensation reaction step (D) without any post-treatment after the completion of the reaction, or alternatively may be used in the subsequent condensation reaction step (D) after isolation/purification by simple and conventional post treatment such as extraction, distillation, or precipitation and, if necessary, separation/isolation by a method such as recrystallization or column chromatography.

Condensation Reaction Step (D)

The condensation reaction step (D) is a step of reacting the quinolone derivative represented by general formula (3) with a halogen compound represented by general formula (4) or an acid anhydride represented by general formula (5) to give a quinoline derivative represented by general formula (6).

Specific examples of halogen compounds represented by general formula (4) include acetyl chloride, propionyl chloride, butanoic acid chloride, cyclopropylcarboxylic chloride, cyclopentylcarboxylic chloride, cyclohexylcarboxylic chloride, n-hexanoic acid chloride, n-octanoic acid chloride, n-nonanoic acid chloride, 2,2-dimethylpropanoic acid chloride, acrylic acid chloride, methacrylic acid chloride, crotonic acid chloride, isocrotonic acid chloride, methyl chloroformate, ethyl chloroformate, isopropyl chloroformate, butyl chloroformate, and octyl chloroformate.

Specific examples of acid anhydrides represented by general formula (5) include acetic anhydride, chloroacetic anhydride, trifluoroacetic anhydride, and cyclohexane carboxylic anhydride.

The condensation reaction step (D) is carried out in the presence or absence of a solvent. The solvent used is not particularly limited, and any solvent may be used as long as the solvent is not detrimental to the reaction. Such solvents include, for example, aliphatic hydrocarbons such as pentane, hexane, heptane, 2-methylbutane, 2-methylpentane, 2-methylhexane, cyclopentane, cyclohexane, and cycloheptane; halogenated aliphatic hydrocarbons such as methylene chloride, chloroform, and dichloroethane; aromatic hydrocarbons such as benzene, toluene, xylene, and mesitylene; halogenated aromatic hydrocarbons such as chlorobenzene and dichlorobenzene; ethers such as diisopropylether, tetrahydrofuran, and dioxane; alcohols such as methanol, ethanol, isopropyl alcohol, 2-butyl alcohol, and t-butyl alcohol; organic carboxylic acids such as acetic acid and propionic acid; amides such as dimethylformamide and dimethylacetamide; and water. The amount of the solvent used is preferably 2 to 50 times by mass, more preferably 3 to 10 times by mass, that of the quinolone derivative. These solvents may be used solely or in a combination of two or more of the solvents.

The condensation reaction step (D) is carried out in the presence or absence of a base. Bases usable herein include, for example, inorganic bases such as carbonates or hydroxides of alkali metals or alkaline earth metals; organic bases such as nitrogen-containing organic bases; metal alkoxides; and metal hydrides. Preferred is potassium carbonate, sodium carbonate, calcium carbonate, sodium hydrogen carbonate, sodium hydroxide, pyridine, triethylamine, sodium methoxide, sodium ethoxide, sodium butoxide, or sodium hydride. The amount of the base used is preferably 0 to 5.0 times by mole, more preferably 0.5 to 2.0 times by mole, that of the quinolone derivative.

In the condensation reaction step (D), preferably, the quinolone derivative is brought into contact with a halogen compound in a liquid phase in the presence of a base. For example, the condensation reaction is carried out, for example, by a method in which, in an inert gas atmosphere under the normal pressure, applied pressure, or reduced pressure, the base, the quinolone derivative, the halogen compound, and the solvent are mixed together, and the mixture is heated with stirring. The reaction temperature is preferably −50 to 100° C., more preferably −10 to 50° C. The quinolone derivative may be used in the form of a salt formed with the base.

The quinoline derivative obtained as a main product by the condensation reaction step (D) as such may be used without any post-treatment after the completion of the reaction, or alternatively may be used after isolation/purification by simple and conventional post treatment such as extraction, distillation, or precipitation and, if necessary, separation/isolation by a method such as recrystallization or column chromatography.

The nitrobenzoic acid derivative represented by general formula (7) may be obtained by subjecting amino group in a compound represented by general formula (10) to substituent replacement according to the following scheme 1.

[Chemical formula 12]

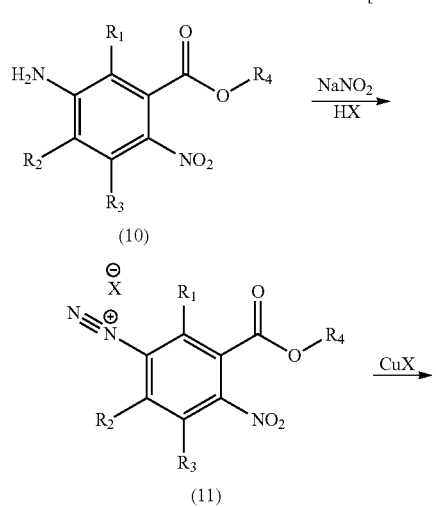

Alternatively, the nitrobenzoic acid derivative represented by general formula (7) may be obtained by nitrating a compound represented by general formula 12 according to the following scheme 2.

[Chemical formula 13]

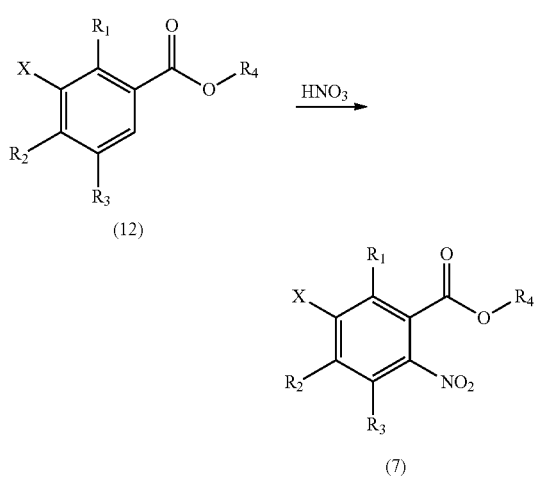

The compound represented by general formula (10) or the compound represented by general formula (12) may be generally purchased.

Specific examples of quinoline derivatives represented by general formula (6) obtained by the process according to the present invention are shown in Table 1 below. These quinoline derivatives are useful as agricultural chemicals or pharmaceutical preparations.

TABLE 1

| Quinoline derivatives | | | | | | | | | | | |
|---|---|---|---|---|---|---|---|---|---|---|---|
| Compound No. | R1 | R2 | R3 | R5 | R6 | R7 | R8 | R9 | R10 | R11 | R12 |
| 1 | H | Me | H | H | H | CF3O | H | H | Et | Me | MeO |
| 2 | Me | Me | H | H | H | CF3O | H | H | Et | Me | MeO |
| 3 | H | Me | H | H | H | CHF2CF2O | H | H | Et | Me | MeO |
| 4 | H | Me | H | H | —OCF2CF2O— | | H | H | Et | Me | MeO |
| 5 | H | Me | H | Cl | H | CF3O | H | H | Et | Me | MeO |
| 6 | H | MeO | H | H | H | CHF2CF2O | H | H | Et | Me | MeO |
| 7 | H | MeO | H | H | —OCF2CF2O— | | H | H | Et | Me | MeO |
| 8 | H | F | H | H | H | CF3O | H | H | Me | Me | MeO |
| 9 | Cl | H | H | H | H | Cl | H | H | Me | Me | Me |
| 10 | H | Cl | H | H | H | Cl | H | H | Me | Me | Me |
| 11 | CF3 | H | H | H | H | CF3O | H | H | Me | Me | Me |
| 12 | H | CF3 | H | H | H | CF3O | H | H | Me | Me | Me |
| 13 | CF3 | H | H | H | H | CF3 | H | Cl | Me | Me | Me |
| 14 | H | CF3 | H | H | H | CF3 | H | Cl | Me | Me | Me |
| 15 | CF3 | H | H | H | H | CF3O | H | H | Et | Me | MeO |
| 16 | H | CF3 | H | H | H | CF3O | H | H | Et | Me | MeO |
| 17 | CF3 | H | H | H | H | CF3 | H | Cl | Me | Me | Me |
| 18 | H | CF3 | H | H | H | CF3O | H | Cl | Me | Me | Me |
| 19 | Cl | H | H | H | H | MeO | H | H | Me | Me | Me |

TABLE 1-continued

Quinoline derivatives

| Compound No. | R1 | R2 | R3 | R5 | R6 | R7 | R8 | R9 | R10 | R11 | R12 |
|---|---|---|---|---|---|---|---|---|---|---|---|
| 20 | H | Cl | H | H | H | MeO | H | H | Me | Me | Me |
| 21 | Me | H | H | H | H | CF3O | H | H | Me | Me | Me |
| 22 | H | Me | H | H | H | CF3O | H | H | Me | Me | Me |
| 23 | Me | Me | H | H | H | CF3O | H | H | Me | Me | Me |
| 24 | CF3 | H | H | H | H | CF3O | H | H | Me | Me | cPr |
| 25 | H | Br | H | H | H | CF3O | H | H | Me | Me | Me |
| 26 | H | Br | H | H | H | CF3O | H | H | Me | Me | MeO |
| 27 | Me | Me | H | H | H | CCl2=CHCH2O | H | H | Et | Me | MeO |
| 28 | Me | Me | H | H | H | ClC≡CCH2O | H | H | Et | Me | MeO |
| 29 | H | MeOCH2 | H | H | H | CF3O | H | H | Et | Me | MeO |
| 30 | MeO | H | MeO | H | H | CF3O | H | H | Et | Me | MeO |
| 31 | H | F | H | H | H | (CF3)2CFS | H | H | Me | Me | MeO |
| 32 | H | F | H | H | H | (CF3)2CFS | H | H | Me | Me | Me |

EXAMPLES

The present invention is further illustrated by the following Examples that are not intended as a limitation of the invention.

Example 1

Synthesis of isopropyl 4-methyl-2-nitro-5-(4-(trifluoromethoxy)phenoxy)benzoate

Dimethylacetamide (716 ml), 170 g of 4-trifluoromethoxyphenol, 246 g of isopropyl 5-chloro-4-methyl-2-nitrobenzoate, and 263.9 g of potassium carbonate were added into a 2000-ml glass flask equipped with a stirring device, a thermometer, and a reflux condenser under a nitrogen atmosphere, and the temperature of the contents of the flask was raised to 100 to 105° C. with stirring. A reaction was allowed to proceed at the same temperature for 37 hr, and 360 ml of dimethylacetamide was then removed by evaporation under the reduced pressure. The reaction solution was poured into 2 L of ice-water, and 1.7 L of ethyl acetate was added thereto. The mixture was stirred and was allowed to stand, followed by separation. The ethyl acetate layer was washed with a 1.5% aqueous sodium hydroxide solution and brine and was concentrated under the reduced pressure to give isopropyl 4-methyl-2-nitro-5-(4-(trifluoromethoxy)phenoxy)benzoate (373.3 g, yield: 97.9%).

Melting point: 47 to 49° C.;
$^1$H-NMR (CDCl$_3$): 1.30 (d, 6H), 2.40 (s, 3H), 5.19 (m, 1H), 6.97 (s, 1H), 7.05 (d, 2H), 7.27 (d, 2H), 7.89 (s, 1H).

Example 2

Synthesis of isopropyl 2-amino-4-methyl-5-(4-(trifluoromethoxy)phenoxy)benzoate

An iron powder (372.9 g), 1290 ml of ethanol, 531 ml of water, and 2.8 g of a 35% hydrochloric acid were charged into a 2000-ml glass flask equipped with a stirring device, a thermometer, and a reflux condenser, and the mixture was heated to reflux. Isopropyl 4-methyl-2-nitro-5-(4-(trifluoromethoxy)phenoxy)benzoate (373 g) dissolved in 398 ml of ethanol was added dropwise thereto over a period of two hr. After reflux for 8 hr, 10 ml of a saturated aqueous sodium bicarbonate solution was added, and the mixture was filtered. The filtrate was concentrated, and 300 ml of ethyl acetate was added to the residue. The mixture was washed with brine, followed by separation. The ethyl acetate layer was concentrated under the reduced pressure. Isopropanol (320 ml) was added to the residue, and the mixture was heated at 70° C. for dissolution. Water (160 ml) was added to the solution to cool the solution. The precipitated solid was collected by filtration and was dried to give isopropyl 2-amino-4-methyl-5-(4-(trifluoromethoxy)phenoxy)benzoate (283.7 g, yield: 82.2%).

Melting point: 71 to 72° C.;
$^1$H-NMR (CDCl$_3$): 1.31 (d, 6H), 2.09 (s, 3H), 5.18 (m, 1H), 5.63 (broad, 2H), 6.56 (s, 1H), 8.82 (d, 2H), 7.12 (d, 2H), 7.50 (s, 1H).

Example 3

Synthesis of isopropyl 2-amino-4-methyl-5-(4-(trifluoromethoxy)phenoxy)benzoate

An 80% methanol (225 g), 50 g of isopropyl 4-methyl-2-nitro-5-(4-(trifluoromethoxy)phenoxy)benzoate, and 2.5 g of a 5% palladium carbon were charged into a 500-ml stainless steel autoclave equipped with a stirring device and a thermometer, and a reaction was allowed to proceed under a hydrogen pressure of 0.5 MPa at 30° C. for 6 hr. After the replacement of the air in the autoclave with nitrogen, the reaction solution was filtered using 220 ml of methanol to remove the catalyst. The methanol solution thus obtained was concentrated under the reduced pressure, and 208 ml of water was added to the residue. The precipitated solid was collected by filtration and was dried to give isopropyl 2-amino-4-methyl-5-(4-(trifluoromethoxy)phenoxy)benzoate (43.96 g, yield: 95%).

Melting point: 71 to 72° C.;
$^1$H-NMR (CDCl$_3$): 1.31 (d, 6H), 2.09 (s, 3H), 5.18 (m, 1H), 5.63 (broad, 2H), 6.56 (s, 1H), 8.82 (d, 2H), 7.12 (d, 2H), 7.50 (s, 1H).

Example 4

Synthesis of 2-ethyl-3,7-dimethyl-6-(4-(trifluoromethoxy)phenoxy)quinolin-4(1H)-one Isopropyl 2-amino-4-methyl-5-(4-(trifluoromethoxy)phenoxy)benzoate (171.4 g), 928 ml of mesitylene, 79.9 g of 3-pentanone, and 16.3 g of benzenesulfonic acid monohydrate were added into a 2000-ml glass flask equipped with a stirring device, a thermometer, a reflux condenser, and a Dean-Stark device under a nitrogen atmosphere, and the temperature was raised to reflux with stirring. A reaction was allowed to proceed for 90 hr while adding benzenesulfonic acid monohydrate in 8.2 g portions eight times. After the completion of the reaction, the reaction solution was cooled to 80° C. Mesitylene (232 ml) and 409 g of a 10% aqueous sodium hydrogen carbonate solution were added to the cooled solution, and the mixture was then cooled to room temperature.

The precipitated crystals were collected on a suction filter, were washed with mesitylene and an aqueous methanol solution, and were dried to give light brown crystals 2-ethyl-3,7-dimethyl-6-(4-(trifluoromethoxy)phenoxy)quinolin-4(1H)-one (119.3 g, yield: 68.1%).

Melting point: 281 to 283° C.;
$^1$H-NMR (DMSO-$d_6$): 1.21 (t, 3H), 1.95 (s, 3H), 2.28 (s, 3H), 2.67 (q, 2H), 7.6 (d, 2H), 7.38 (d, 2H), 7.43 (s, 2H), 11.37 (s, 1H).

Example 5

Synthesis of 2-ethyl-3,7-dimethyl-6-(4-(trifluoromethoxy)phenoxy)quinolin-4(1H)-one Isopropyl 2-amino-4-methyl-5-(4-(trifluoromethoxy)phenoxy)benzoate (3.69 g), 20 ml of xylene, 5.3 ml of 3-pentanone, and 0.256 g of zinc chloride were added into a 50-ml glass flask equipped with a stirring device, a thermometer, a reflux condenser, and a Dean-Stark device under a nitrogen atmosphere, and the temperature was raised to reflux with stirring. A reaction was allowed to proceed for 50 hr while adding 1.1 g of zinc chloride in four divided portions. After the completion of the reaction, the mixture was cooled to 70° C., and 10 ml of 0.1 N hydrochloric acid was added to the cooled solution, followed by cooling to room temperature. The precipitated solid was collected on a suction filter, was washed with an aqueous methanol solution and distilled water, and was dried to give 2-ethyl-3,7-dimethyl-6-(4-(trifluoromethoxy)phenoxy)quinolin-4(1H)-one as a light brown solid (3.29 g, yield: 87.3%).

Melting point: 281 to 283° C.;
$^1$H-NMR (DMSO-$d_6$): 1.21 (t, 3H), 1.95 (s, 3H), 2.28 (s, 3H), 2.67 (q, 2H), 7.6 (d, 2H), 7.38 (d, 2H), 7.43 (s, 2H), 11.37 (s, 1H).

Example 6

Synthesis of 2-ethyl-3,7-dimethyl-6-(4-(trifluoromethoxy)phenoxy)quinolin-4-yl methyl carbonate Dimethylacetamide (694 ml), 35.2 g of sodium t-butoxide, and 131 g of 2-ethyl-3,7-dimethyl-6-(4-(trifluoromethoxy)phenoxy)quinolin-4(1H)-one were added into a 1000-ml glass flask equipped with a stirring device, a thermometer, and a reflux condenser under a nitrogen atmosphere, and the mixture was stirred at room temperature. Methyl chloroformate (34.4 g) was added dropwise thereto, and a reaction was allowed to proceed at room temperature for one hr. The reaction mixture was poured into 1735 ml of water contained in a 5-L plastic container, and the mixture was stirred at room temperature for two hr. The precipitated solid was collected by filtration through a suction filter and was washed with water. The solid was dried under the reduced pressure to give 2-ethyl-3,7-dimethyl-6-(4-(trifluoromethoxy)phenoxy)quinolin-4-yl methyl carbonate (149.5 g, yield: 98.8%). The results of $^1$H-NMR analysis showed that the compound thus obtained was No. 120 described in a brochure of International Publication No. 2006/013896.

$^1$H-NMR (CDCl$_3$): 1.38 (t, 3H), 2.31 (s, 3H), 2.41 (s, 3H), 3.01 (q, 2H), 3.88 (s, 3H), 6.97 (d, 2H), 7.14 (s, 1H), 7.20 (d, 2H), 7.94 (s, 1H).

Example 7

Synthesis of 2-ethyl-3,7-dimethyl-6-(4-(trifluoromethoxy)phenoxy)quinolin-4(1H)-one Xylene (542 ml) and 51.5 g of p-toluenesulfonic acid monohydrate were charged into a 1000-ml glass flask equipped with a stirring device, a thermometer, a reflux condenser, and a Dean-Stark device under a nitrogen atmosphere, and water was removed from the mixture under reflux for 40 min. The mixture was then cooled to 110° C., and 100 g of isopropyl 2-amino-4-methyl-5-(4-(trifluoromethoxy)phenoxy)benzoate and 11.7 g of 3-pentanone were added to the cooled solution. Water was removed from the reaction solution under reflux. P-toluenesulfonic acid monohydrate (46.4 g) and 34.9 g of 3-pentanone were added in divided portions, and a reaction was allowed to proceed for 107 hr. After the completion of the reaction, the mixture was cooled to 80° C., 496 g of a 10% aqueous sodium hydrogen carbonate solution was added thereto, and the mixture was cooled to room temperature. The precipitated solid was collected on a suction filter, was washed with 130 ml of xylene and 260 ml of a 50% aqueous methanol solution, and was dried to give 2-ethyl-3,7-dimethyl-6-(4-(trifluoromethoxy)phenoxy)quinolin-4(1H)-one as a light brown solid (83.3 g, yield: 81.5%).

Melting point: 281 to 283° C.;
$^1$H-NMR (DMSO $d_6$): 1.21 (t, 3H), 1.95 (s, 3H), 2.28 (s, 3H), 2.67 (q, 2H), 7.6 (d, 2H), 7.38 (d, 2H), 7.43 (s, 2H), 11.37 (s, 1H).

Example 8

Synthesis of 2-ethyl-3,7-dimethyl-6-(4-(trifluoromethoxy)phenoxy)quinolin-4-yl methyl carbonate Dimethylformamide (980 ml) and 98 g of 2-ethyl-3,7-dimethyl-6-(4-(trifluoromethoxy)phenoxy)quinolin-4(1H)-one were charged into a 2000-ml glass flask equipped with a stirring device, a thermometer, a reflux condenser, and a calcium chloride tube under a nitrogen atmosphere, and the temperature of the contents of the flask was cooled to 15° C. A 55% sodium hydride (18.2 g) was added thereto, and a reaction was allowed to proceed at 15 to 20° C. for one hr. Methyl chloroformate (32.1 g) was added dropwise into the reaction solution, and a reaction was allowed to proceed at room temperature for one hr. The reaction mixture was poured into 5 L of ice-water contained in the a 10-L plastic container, and the mixture was stirred at room temperature for two hr. The precipitated solid was collected by filtration through a suction filter and was washed with water and n-hexane. The solid was dried under the reduced pressure to give 2-ethyl-3,7-dimethyl-6-(4-(trifluoromethoxy)phenoxy)quinolin-4-yl methyl carbonate (103.3 g, yield: 91.4%). The results of $^1$H-NMR analysis showed that the compound thus obtained was No. 120 described in a brochure of International Publication No. 2006/013896.

$^1$H-NMR (CDCl$_3$): 1.38 (t, 3H), 2.31 (s, 3H), 2.41 (s, 3H), 3.01 (q, 2H), 3.88 (s, 3H), 6.97 (d, 2H), 7.14 (s, 1H), 7.20 (d, 2H), 7.94 (s, 1H).

Example 9

Synthesis of 2-ethyl-3,7-dimethyl-6-(4-(trifluoromethoxy)phenoxy)quinolin-4(1H)-one Aluminum chloride (30.0 g) and 125 ml of xylene were added into a 1000-ml glass flask equipped with a stirring device, a thermometer, a reflux condenser, and Dean-Stark device under a nitrogen gas stream. 3-Pentanone (58.1 g) was added dropwise thereto with stirring at 10° C. or below. Subsequently, 60.55 g of isopropyl 2-amino-4-methyl-5-(4-(trifluoromethoxy)phenoxy)benzoate dissolved in 250 ml of xylene was added dropwise thereto at room temperature, and the mixture was heated under reflux for 6 hr. A mixture composed of 5.0 g of aluminum chloride, 65 ml of xylene, and 9.69 g of 3-pentanone was added into the reaction solution, and the mixture was further heated under reflux for 18 hr. After the completion of the reaction, the reaction solution was allowed to cool at room temperature. The reaction solution was added little by little to 150 ml of a 5% aqueous hydrochloric acid solution prepared in a separate 1000-ml glass flask. Further, 150 ml of methanol was added thereto, and the mixture was heated under reflux for about one hr. The reaction mixture was allowed to cool at room temperature and was collected on a suction filter. The reaction mixture was washed with an aqueous methanol solution and was dried to give 2-ethyl-3,7-dimethyl-6-(4-(trifluoromethoxy)phenoxy) quinolin-4(1H)-one as a light brown solid (51.33 g, yield: 90.7%).

Melting point: 281 to 283° C.;

$^1$H-NMR (DMSO-$d_6$): 1.21 (t, 3H), 1.95 (s, 3H), 2.28 (s, 3H), 2.67 (q, 2H), 7.6 (d, 2H), 7.38 (d, 2H), 7.43 (s, 2H), 11.37 (s, 1H).

EFFECT OF THE INVENTION

When a target compound was produced by a conventional production process described in a brochure of International Publication No. 2006/013896 in which a 6-aryloxyquinoline derivative is obtained from a substituted aniline in two steps, the overall yield of the target compound was low to medium, and was approximately 6 to 58%. Further, when a 5- or 7-substituted 6-aryloxyquinoline derivative is produced, the isolated yield was as low as 6 to 44%. Furthermore, since the 5-substituted or 7-substituted 6-aryloxyquinoline derivative is not obtained as a single product, a complicated separation/purification step, for example, using column chromatography is required and, thus, there is room for improvement in the production thereof on a commercial scale.

By contrast, in a production process of a 6-aryloxyquinoline derivative according to the present invention, a 6-aryloxyquinoline derivative of general formula (6) as a target compound can be produced from a nitrobenzoic acid derivative of general formula (7) in four steps. In each of the reaction steps, there is no need to adopt special reaction apparatus and reaction conditions, and the optimization of reaction conditions could provide a high reaction yield of 80 to 99% in terms of each element step. As a result, the 6-aryloxyquinoline derivative as the target compound could be obtained at a high yield of 56 to 66% in terms of an overall (four steps) yield using a nitrobenzoate of general formula (7) as a starting compound. Further, in the 6-aryloxyquinoline derivative, at the same time, a compound having a substituent at 5- or 7-position is also obtained as a single product. Accordingly, a complicated isolation/purification step is not necessary, and, thus, a significant reduction in number of necessary production steps can be realized.

That is, according to the above Examples, the process for producing a 6-aryloxyquinoline derivative according to the present invention can realize a high reaction efficiency and relies upon a quinoline ring construction reaction involving regioselective substituent introduction, demonstrating that the production process is a production process of a 6-aryloxyquinoline derivative that can realize a high yield and is industrially advantageous.

The invention claimed is:

1. A process for producing a quinoline derivative, the process comprising:
   (i) a cyclization reaction step (C) of reacting an anthranilic acid derivative represented by general formula (1):
   wherein
   $R_1$, $R_2$, and $R_3$ each independently represent a hydrogen atom, a halogen atom, $C_{1-4}$ alkyl optionally substituted by a halogen atom(s), or $C_{1-4}$ alkoxy optionally substituted by a halogen atom(s), provided that $R_1$, $R_2$, and $R_3$ do not simultaneously represent a hydrogen atom,
   $R_4$ represents a hydrogen atom or a protecting group of carboxylic acid, and
   $R_5$, $R_6$, $R_7$, $R_8$, and $R_9$ each independently represent a hydrogen atom, a halogen atom, $C_{1-8}$ alkyl optionally substituted by a halogen atom(s), $C_{1-8}$ alkoxy optionally substituted by a halogen atom(s), $C_{1-8}$ alkylthio optionally substituted by a halogen atom(s), $C_{2-4}$ alkenyloxy optionally substituted by a halogen atom(s), $C_{2-4}$ alkenylthio optionally substituted by a halogen atom(s), or $C_{2-4}$ alkynyloxy optionally substituted by a halogen atom(s),
   or any two adjacent substituents of $R_5$, $R_6$, $R_7$, $R_8$, and $R_9$ together represent —O—$(CH_2)_n$—O— wherein n is 1 or 2, optionally substituted by one or more halogen atoms,
   with a ketone represented by general formula (2):
   wherein $R_{10}$ and $R_{11}$ each independently represent a hydrogen atom or $C_{1-4}$ alkyl optionally substituted by a halogen atom(s),
   or $R_{10}$ and $R_{11}$ together represent —$(CH_2)_m$— wherein m is 3 or 4, provided that $R_{10}$ and $R_{11}$ do not simultaneously represent a hydrogen atom,
   in the presence of an acid to obtain a quinolone derivative of general formula (3):
   wherein $R_1$, $R_2$, $R_3$, $R_5$, $R_6$, $R_7$, $R_8$, $R_9$, $R_{10}$, and $R_{11}$ are as defined above; and
   (ii) a condensation reaction step (D) of reacting the quinolone derivative of general formula (3) with a halogen compound represented by general formula (4):
   wherein $R_{12}$ represents $C_{1-8}$ alkyl optionally substituted by a halogen atom(s), $C_{3-6}$ cyclic alkyl optionally substituted by a halogen atom(s), $C_{2-4}$ alkenyl optionally substituted by a halogen atom(s), $OR_{13}$ wherein $R_{13}$ represents $C_{1-8}$ alkyl optionally substituted by a halogen atom(s); $C_{3-6}$ cyclic alkyl optionally substituted by a halogen atom(s); or $C_{2-4}$ alkenyl optionally substituted by a halogen atom(s), or $SR_{14}$ wherein $R_{14}$ represents $C_{1-8}$ alkyl optionally substituted by a halogen atom(s); $C_{3-6}$ cyclic alkyl optionally substituted by a halogen atom(s); or $C_{2-4}$ alkenyl optionally substituted by a halogen atom(s), and
   Y represents any one of fluorine, chlorine, bromine, and iodine,
   or an acid anhydride represented by general formula (5):
   wherein $R_{12}$ is as defined above,
   to obtain a quinoline derivative represented by general formula (6):
   wherein $R_1$, $R_2$, $R_3$, $R_5$, $R_6$, $R_7$, $R_8$, $R_9$, $R_{10}$, $R_{11}$, and $R_{12}$ are as defined above.

2. The process according to claim 1, wherein $R_4$ represents a hydrogen atom, $C_{1-8}$ alkyl optionally substituted by a halogen atom(s) or optionally substituted by $C_{1-4}$ alkoxy optionally substituted by a halogen atom(s), $C_{3-8}$ cyclic alkyl optionally substituted by a halogen atom(s), $C_{1-4}$ alkoxymethyl, benzoylmethyl optionally substituted by a halogen atom(s), or $C_{7-14}$ aralkyl optionally substituted by a halogen atom(s), $C_{1-4}$ alkyl, or $C_{1-4}$ alkoxy.

3. The process according to claim 1, wherein $R_1$, $R_2$, and $R_3$ each independently represent a hydrogen atom, a chlorine atom, a bromine atom, a fluorine atom, methyl, ethyl, methoxy, ethoxy, or trifluoromethyl, provided that $R_1$, $R_2$, and $R_3$ do not simultaneously represent a hydrogen atom; $R_4$ represents $C_{1-8}$ alkyl optionally substituted by a halogen atom(s) or optionally substituted by $C_{1-4}$ alkoxy optionally substituted by a halogen atom(s), $C_{3-8}$ cyclic alkyl optionally substituted by a halogen atom(s), or $C_{7-14}$ aralkyl optionally substituted by a halogen atom(s), $C_{1-4}$ alkyl, or $C_{1-4}$ alkoxy; $R_5$, $R_6$, $R_7$, $R_8$, and $R_9$ each independently represent a hydrogen atom, a chlorine atom, a bromine atom, a fluorine atom, methyl, ethyl, methoxy, ethoxy, trifluoromethyl, pentafluoroethyl, trifluoromethoxy, or 1,1,2,2-tetrafluoroethoxy, or $R_6$ and $R_7$ together represent —$OCF_2CF_2O$—; $R_{10}$ and $R_{11}$ each independently represent a hydrogen atom or $C_{1-4}$ alkyl optionally substituted by a halogen atom(s), provided that $R_{10}$ and $R_{11}$ do not simultaneously represent a hydrogen atom; and $R_{12}$ represents $C_{1-4}$ alkyl optionally substituted by a halogen atom(s) or $OR_{13}$ wherein $R_{13}$ represents $C_{1-4}$ alkyl optionally substituted by a halogen atom(s).

4. The process according to claim 1, wherein any one of $R_1$, $R_2$, and $R_3$ represents methyl, ethyl, or trifluoromethyl with the other two representing a hydrogen atom, $R_4$ represents $C_{1-4}$ alkyl optionally substituted by a halogen atom(s), any one of $R_5$, $R_6$, $R_7$, $R_8$, and $R_9$ represents methoxy, ethoxy, trifluoromethoxy, or 1,1,2,2-tetrafluoroethoxy with the other four representing a hydrogen atom, $R_{10}$ and $R_{11}$ each independently represent $C_{1-4}$ alkyl optionally substituted by a halogen atom(s), and $R_{12}$ represents $OR_{13}$ wherein $R_{13}$ represents $C_{1-4}$ alkyl.

5. The process according to claim 1, wherein $R_{10}$ represents —$CH_2$—$R_{15}$, $R_{11}$ represents $R_{15}$, and $R_{15}$ represents $C_{1-3}$ alkyl.

6. The process according to claim 1, wherein the acid used in the cyclization reaction step (C) is an organic sulfonic acid or Lewis acid.

7. The process according to claim 6, wherein the organic sulfonic acid is benzenesulfonic acid or p-toluenesulfonic acid.

8. The process according to claim 6, wherein the Lewis acid is zinc chloride, iron chloride, titanium chloride, or aluminum chloride.

9. An anthranilic acid derivative represented by general formula (1a):
wherein
any one of $R_{1a}$, $R_{2a}$, and $R_{3a}$ represents $C_{1-4}$ alkyl optionally substituted by a halogen atom(s) with the other two representing a hydrogen atom,
$R_{4a}$ represents $C_{1-4}$ alkyl optionally substituted by a halogen atom(s), and
any one of $R_{5a}$, $R_{6a}$, $R_{7a}$, $R_{8a}$, and $R_{9a}$ represents $C_{1-8}$ alkoxy optionally substituted by a halogen atom(s) with the other four representing a hydrogen atom.

10. A process for producing an anthranilic acid derivative, the process comprising:
(i) an etherification step (A) of reacting a nitrobenzoic acid derivative represented by general formula (7):
wherein
$R_1$, $R_2$, and $R_3$ each independently represent a hydrogen atom, a halogen atom, $C_{1-4}$ alkyl optionally substituted by a halogen atom(s), or $C_{1-4}$ alkoxy optionally substituted by a halogen atom(s), provided that $R_1$, $R_2$, and $R_3$ do not simultaneously represent a hydrogen atom,
$R_4$ represents a hydrogen atom or a protecting group of carboxylic acid, and
X represents any one of fluorine, chlorine, bromine, and iodine,
with a phenol derivative represented by general formula (8):
wherein
$R_5$, $R_6$, $R_7$, $R_8$, and $R_9$ each independently represent a hydrogen atom, a halogen atom, $C_{1-8}$ alkyl optionally substituted by a halogen atom(s), $C_{1-8}$ alkoxy optionally substituted by a halogen atom(s), $C_{1-8}$ alkylthio optionally substituted by a halogen atom(s), $C_{2-4}$ alkenyloxy optionally substituted by a halogen atom(s), $C_{2-4}$ alkenylthio optionally substituted by a halogen atom(s), or $C_{2-4}$ alkynyloxy optionally substituted by a halogen atom(s),
or any two adjacent substituents of $R_5$, $R_6$, $R_7$, $R_8$, and $R_9$ together represent —O—$(CH_2)_n$—O—, wherein n is 1 or 2, optionally substituted by one or more halogen atoms,
in the presence or absence of a base to obtain an ether derivative represented by general formula (9):
wherein $R_1$, $R_2$, $R_3$, $R_4$, $R_5$, $R_6$, $R_7$, $R_8$, and $R_9$ are as defined above; and
(ii) a reduction step (B) of reducing the ether derivative of general formula (9) to obtain an anthranilic acid derivative represented by general formula (1):
wherein $R_1$, $R_2$, $R_3$, $R_4$, $R_5$, $R_6$, $R_7$, $R_8$, and $R_9$ are as defined above.

11. The process according to claim 10, wherein $R_4$ represents a hydrogen atom, $C_{1-8}$ alkyl optionally substituted by a halogen atom(s) or optionally substituted by $C_{1-4}$ alkoxy optionally substituted by a halogen atom(s), $C_{3-8}$ cyclic alkyl optionally substituted by a halogen atom(s), $C_{1-4}$ alkoxymethyl, benzoylmethyl optionally substituted by a halogen atom(s), or $C_{7-14}$ aralkyl optionally substituted by a halogen atom(s), $C_{1-4}$ alkyl, or $C_{1-4}$ alkoxy.

12. The process according to claim 10, wherein $R_1$, $R_2$, and $R_3$ each independently represent a hydrogen atom, a chlorine atom, a bromine atom, a fluorine atom, methyl, ethyl, methoxy, ethoxy, or trifluoromethyl, provided that $R_1$, $R_2$, and $R_3$ do not simultaneously represent a hydrogen atom; $R_4$ represents $C_{1-8}$ alkyl optionally substituted by a halogen atom(s) or optionally substituted by $C_{1-4}$ alkoxy optionally substituted by a halogen atom(s), $C_{3-8}$ cyclic alkyl optionally substituted by a halogen atom(s), or $C_{7-14}$ aralkyl optionally substituted by a halogen atom(s), $C_{1-4}$ alkyl, or $C_{1-4}$ alkoxy; and $R_5$, $R_6$, $R_7$, $R_8$, and $R_9$ each independently represent a hydrogen atom, a chlorine atom, a bromine atom, a fluorine atom, methyl, ethyl, methoxy, ethoxy, trifluoromethyl, pentafluoroethyl, trifluoromethoxy, or 1,1,2,2-tetrafluoroethoxy, or $R_6$ and $R_7$ together represent —$OCF_2CF_2O$—.

13. The process according to claim 10, wherein any one of $R_1$, $R_2$, and $R_3$ represents methyl, ethyl, or trifluoromethyl with the other two representing a hydrogen atom, $R_4$ represents $C_{1-4}$ alkyl optionally substituted by a halogen atom(s), and any one of $R_5$, $R_6$, $R_7$, $R_8$, and $R_9$ represents methoxy, ethoxy, trifluoromethoxy, or 1,1,2,2-tetrafluoroethoxy with the other four representing a hydrogen atom.

14. The process according to claim 10, wherein the reduction in the reduction step (B) is carried out by either hydrogenation in the presence of palladium, or using iron powder.

15. A process for producing a quinoline derivative, the process comprising:

(i) an etherification step (A) of reacting a nitrobenzoic acid derivative represented by general formula (7):
wherein
$R_1$, $R_2$, and $R_3$ each independently represent a hydrogen atom, a halogen atom, $C_{1-4}$ alkyl optionally substituted by a halogen atom(s), or $C_{1-4}$ alkoxy optionally substituted by a halogen atom(s), provided that $R_1$, $R_2$, and $R_3$ do not simultaneously represent a hydrogen atom,
$R_4$ represents a hydrogen atom or a protecting group of carboxylic acid, and
X represents any one of fluorine, chlorine, bromine, and iodine,
with a phenol derivative represented by general formula (8):
wherein
$R_5$, $R_6$, $R_7$, $R_8$, and $R_9$ each independently represent a hydrogen atom, a halogen atom, $C_{1-8}$ alkyl optionally substituted by a halogen atom(s), $C_{1-8}$ alkoxy optionally substituted by a halogen atom(s), $C_{1-8}$ alkylthio optionally substituted by a halogen atom(s), $C_{2-4}$ alkenyloxy optionally substituted by a halogen atom(s), $C_{2-4}$ alkenylthio optionally substituted by a halogen atom(s), or $C_{2-4}$ alkynyloxy optionally substituted by a halogen atom(s),
or any two adjacent substituents of $R_5$, $R_6$, $R_7$, $R_8$, and $R_9$ together represent —O—$(CH_2)_n$—O—, wherein n is 1 or 2, optionally substituted by one or more halogen atoms,
in the presence or absence of a base to obtain an ether derivative represented by general formula (9):
wherein $R_1$, $R_2$, $R_3$, $R_4$, $R_5$, $R_6$, $R_7$, $R_8$, and $R_9$ are as defined above;

(ii) a reduction step (B) of reducing the ether derivative of general formula (9) to obtain an anthranilic acid derivative represented by general formula (1):
wherein $R_1$, $R_2$, $R_3$, $R_4$, $R_5$, $R_6$, $R_7$, $R_8$, and $R_9$ are as defined above;

(iii) a cyclization reaction step (C) of reacting an anthranilic acid derivative represented by general formula (1) with a ketone represented by general formula (2):
wherein $R_{10}$ and $R_{11}$ each independently represent a hydrogen atom or $C_{1-4}$ alkyl optionally substituted by a halogen atom(s),
or $R_{10}$ and $R_{11}$ together represent —$(CH_2)_m$— wherein m is 3 or 4, provided that $R_{10}$ and $R_{11}$ do not simultaneously represent a hydrogen atom,
in the presence of an acid to obtain a quinolone derivative of general formula (3):
wherein $R_1$, $R_2$, $R_3$, $R_5$, $R_6$, $R_7$, $R_8$, $R_9$, $R_{10}$, and $R_{11}$ are as defined above; and (iv) a condensation reaction step (D) of reacting the quinolone derivative of general formula (3) with a halogen compound represented by general formula (4):
wherein $R_{12}$ represents $C_{1-8}$ alkyl optionally substituted by a halogen atom(s), $C_{3-6}$ cyclic alkyl optionally substituted by a halogen atom(s), $C_{2-4}$ alkenyl optionally substituted by a halogen atom(s), $OR_{13}$ wherein $R_{13}$ represents $C_{1-8}$ alkyl optionally substituted by a halogen atom(s); $C_{3-6}$ cyclic alkyl optionally substituted by a halogen atom(s); or $C_{2-4}$ alkenyl optionally substituted by a halogen atom(s), or $SR_{14}$ wherein $R_{14}$ represents $C_{1-8}$ alkyl optionally substituted by a halogen atom(s); $C_{3-6}$ cyclic alkyl optionally substituted by a halogen atom(s); or $C_{2-4}$ alkenyl optionally substituted by a halogen atom(s), and
Y represents any one of fluorine, chlorine, bromine, and iodine, or an acid anhydride represented by general formula (5):
wherein $R_{12}$ is as defined above,
to obtain a quinoline derivative represented by general formula (6):
wherein $R_1$, $R_2$, $R_3$, $R_5$, $R_6$, $R_7$, $R_8$, $R_9$, $R_{10}$, $R_{11}$, and $R_{12}$ are as defined above.

16. The process according to claim 15, wherein $R_4$ represents a hydrogen atom, $C_{1-8}$ alkyl optionally substituted by a halogen atom(s) or optionally substituted by $C_{1-4}$ alkoxy optionally substituted by a halogen atom(s), $C_{3-8}$ cyclic alkyl optionally substituted by a halogen atom(s), $C_{1-4}$ alkoxymethyl, benzoylmethyl optionally substituted by a halogen atom(s), or $C_{7-14}$ aralkyl optionally substituted by a halogen atom(s), $C_{1-4}$ alkyl, or $C_{1-4}$ alkoxy.

17. The process according to claim 15, wherein $R_1$, $R_2$, and $R_3$ each independently represent a hydrogen atom, a chlorine atom, a bromine atom, a fluorine atom, methyl, ethyl, methoxy, ethoxy, or trifluoromethyl, provided that $R_1$, $R_2$, and $R_3$ do not simultaneously represent a hydrogen atom; $R_4$ represents $C_{1-8}$ alkyl optionally substituted by a halogen atom(s) or optionally substituted by $C_{1-4}$ alkoxy optionally substituted by a halogen atom(s), $C_{3-8}$ cyclic alkyl optionally substituted by a halogen atom(s), or $C_{7-14}$ aralkyl optionally substituted by a halogen atom(s), $C_{1-4}$ alkyl, or $C_{1-4}$ alkoxy; $R_5$, $R_6$, $R_7$, $R_8$, and $R_9$ each independently represent a hydrogen atom, a chlorine atom, a bromine atom, a fluorine atom, methyl, ethyl, methoxy, ethoxy, trifluoromethyl, pentafluoroethyl, trifluoromethoxy, or 1,1,2,2-tetrafluoroethoxy, or $R_6$ and $R_7$ together represent —$OCF_2CF_2O$—; $R_{10}$ and $R_{11}$ each independently represent a hydrogen atom or $C_{1-4}$ alkyl optionally substituted by a halogen atom(s), provided that $R_{10}$ and $R_{11}$ do not simultaneously represent a hydrogen atom; and $R_{12}$ represents $C_{1-4}$ alkyl optionally substituted by a halogen atom(s) or $OR_{13}$ wherein $R_{13}$ represents $C_{1-4}$ alkyl optionally substituted by a halogen atom(s).

18. The process according to claim 15, wherein any one of $R_1$, $R_2$, and $R_3$ represents methyl, ethyl, or trifluoromethyl with the other two representing a hydrogen atom, $R_4$ represents $C_{1-4}$ alkyl optionally substituted by a halogen atom(s), any one of $R_5$, $R_6$, $R_7$, $R_8$, and $R_9$ represents methoxy, ethoxy, trifluoromethoxy, or 1,1,2,2-tetrafluoroethoxy with the other four representing a hydrogen atom, $R_{10}$ and $R_{11}$ each independently represent $C_{1-4}$ alkyl optionally substituted by a halogen atom(s), and $R_{12}$ represents $OR_{13}$ wherein $R_{13}$ represents $C_{1-4}$ alkyl.

19. The process according to claim 15, wherein $R_{10}$ represents —$CH_2$—$R_{15}$, $R_{11}$ represents $R_{15}$, and $R_{15}$ represents $C_{1-3}$ alkyl.

20. The process according to claim 15, wherein the reduction in the reduction step (B) is carried out either by hydrogenation in the presence of palladium, or using iron powder.

21. The process according to claim 15, wherein the acid used in the cyclization reaction step (C) is an organic sulfonic acid or Lewis acid.

22. The process according to claim 21, wherein the organic sulfonic acid is benzenesulfonic acid or p-toluenesulfonic acid.

23. The process according to claim 21, wherein the Lewis acid is zinc chloride, iron chloride, titanium chloride, or aluminum chloride.

* * * * *